(12) United States Patent
Dicharry et al.

(10) Patent No.: US 10,790,069 B2
(45) Date of Patent: Sep. 29, 2020

(54) DELIVERING RADIATION

(71) Applicant: SOURCE PRODUCTION & EQUIPMENT CO., INC., St. Rose, LA (US)

(72) Inventors: Richard Donald Dicharry, St. Rose, LA (US); William Kirk Miller, Jr., St. Rose, LA (US); Steven Andrew Johnson, Louisiana, LA (US)

(73) Assignee: SOURCE PRODUCTION & EQUIPMENT CO., INC., St. Rose, LA (US)

( * ) Notice: Subject to any disclaimer, the term of this patent is extended or adjusted under 35 U.S.C. 154(b) by 0 days.

(21) Appl. No.: 16/340,192

(22) PCT Filed: Oct. 11, 2017

(86) PCT No.: PCT/US2017/056140
§ 371 (c)(1),
(2) Date: Apr. 8, 2019

(87) PCT Pub. No.: WO2018/071542
PCT Pub. Date: Apr. 19, 2018

(65) Prior Publication Data
US 2019/0267146 A1 Aug. 29, 2019

Related U.S. Application Data

(60) Provisional application No. 62/420,106, filed on Nov. 10, 2016, provisional application No. 62/406,670, filed on Oct. 11, 2016.

(51) Int. Cl.
*G21F 5/015* (2006.01)
*A61B 6/10* (2006.01)
(Continued)

(52) U.S. Cl.
CPC .............. *G21F 5/015* (2013.01); *A61B 6/107* (2013.01); *G21F 1/125* (2013.01); *G21F 3/00* (2013.01); *A61B 6/4258* (2013.01); *G03B 42/02* (2013.01)

(58) Field of Classification Search
None
See application file for complete search history.

(56) References Cited

U.S. PATENT DOCUMENTS

| 2,976,423 A | * | 3/1961 | Prest | G21F 7/005 |
| | | | | 250/497.1 |
| 3,032,661 A | * | 5/1962 | Wolf | A61N 5/10 |
| | | | | 250/497.1 |
| 3,147,383 A | * | 9/1964 | Prest | G21F 5/02 |
| | | | | 250/515.1 |

(Continued)

FOREIGN PATENT DOCUMENTS

| EP | 0 513 515 A2 | 11/1992 |
| EP | 0513515 A2 * | 11/1992 |

(Continued)

*Primary Examiner* — Andrew Smyth
(74) *Attorney, Agent, or Firm* — Muirhead and Saturnelli, LLC

(57) ABSTRACT

A radiography camera system includes an exposure container made from radiation shielding material and having a curved channel therein that terminates inside the exposure container, a first conduit portion having a first end coupled to the exposure container, a switch coupled to a second end the first conduit portion, a second conduit portion having a first end coupled to the switch, a guide tube coupled to the switch, a crank coupled to a second end of the second conduit portion, and a cable disposed in the crank and having a connector for a source assembly on an end thereof, the cable actuating the switch to cause the cable to feed through one of: the first conduit portion or the guide tube when the crank unwinds the cable. The exposure container may be made from depleted uranium, tungsten, and/or lead. The curved channel may be J-shaped.

17 Claims, 23 Drawing Sheets

(51) Int. Cl.
*G21F 1/12* (2006.01)
*G21F 3/00* (2006.01)
*A61B 6/00* (2006.01)
*G03B 42/02* (2006.01)

(56) References Cited

U.S. PATENT DOCUMENTS

| | | | | |
|---|---|---|---|---|
| 3,393,317 | A * | 7/1968 | Spencer | G21F 5/02 |
| | | | | 250/497.1 |
| 3,593,594 | A * | 7/1971 | Perry | G21F 5/02 |
| | | | | 250/497.1 |
| 4,211,928 | A * | 7/1980 | Parsons, Jr. | G21F 5/02 |
| | | | | 250/497.1 |
| 4,220,864 | A * | 9/1980 | Sauerwein | G21F 5/02 |
| | | | | 250/496.1 |
| 4,281,252 | A * | 7/1981 | Parsons, Jr. | G21F 5/02 |
| | | | | 250/497.1 |
| 5,065,033 | A * | 11/1991 | Parsons | G21F 5/02 |
| | | | | 250/497.1 |
| 5,418,379 | A * | 5/1995 | Parsons | G21F 5/02 |
| | | | | 250/497.1 |
| 6,875,377 | B1 * | 4/2005 | Shilton | G21G 4/06 |
| | | | | 250/390.01 |
| 8,270,567 | B2 * | 9/2012 | Yamamoto | H01J 31/28 |
| | | | | 378/62 |
| 8,357,316 | B2 * | 1/2013 | Munro, III | G21G 4/04 |
| | | | | 252/645 |
| 2010/0128845 | A1 * | 5/2010 | Yamamoto | H01L 27/14676 |
| | | | | 378/62 |
| 2013/0009120 | A1 * | 1/2013 | Munro, III | G21G 4/06 |
| | | | | 252/625 |
| 2014/0066687 | A1 * | 3/2014 | Munro, III | A61N 5/1081 |
| | | | | 600/1 |
| 2015/0208493 | A1 * | 7/2015 | Cole | G21F 5/02 |
| | | | | 378/197 |

FOREIGN PATENT DOCUMENTS

EP 0513515 A3 * 12/1993
EP 0513515 B1 * 7/1997

* cited by examiner

DELIVERING RADIATION

CROSS-REFERENCE TO RELATED APPLICATIONS

This application claims priority to U.S. provisional patent application No. 62/406,670 filed on Oct. 11, 2016 and titled "DELIVERING RADIATION" and on U.S. provisional patent application No. 62/420,106 filed on Nov. 10, 2016 and titled "DELIVERING RADIATION", both of which are incorporated by reference herein.

TECHNICAL FIELD

This application relates to the field of radiography and the application of radiation, and more particularly to the field of manipulating a source in connection with the application of radiation.

BACKGROUND OF THE INVENTION

In radiography, a source of penetrating photon radiation (X-ray or gamma ray) is placed on one side of a specimen and a detector of radiation (often film, but many types of detectors are used) is placed on the other side. In passing through the specimen, the radiation is attenuated by the material along the beam path. Thicker and denser material will attenuate the radiation to a greater degree than thinner and less dense material. Therefore, when a source of radiation is placed at a distance from the object to be examined, the radiation detector will produce a spatial image of the thickness and density variations along all of the beam paths through the object.

The first radiographs were made in 1895 with the discovery of X-rays by Wilhelm Conrad Röntgen, a German physicist. X-rays are produced when high energy electrons collide with a metal target within a vacuum. The electrons are energized by accelerating them through a high voltage electric field. In most X-ray systems, the target is made from Tungsten, although other target materials, such as molybdenum, may also be used. The penetrability of the photon radiation is dependent upon the energy of the photon. Lower energy photons will be more highly attenuated (and therefore penetrate less) than higher energy photons. Therefore, for radiographic examination of thick specimens of dense material, high energy photons are required.

Normal X-ray generators are limited in the energy that can be produced because of limitations in the voltage that can practicably be applied to the X-ray tube. Furthermore, a typical X-ray machine is large and requires a power source, it cannot be taken to remote locations without significant expense. However, radioisotope sources can have far higher photon energies than could be obtained from normal X-ray generators. Radioisotope sources also have the advantage of not requiring an external power source. Therefore, industrial radiography performed with gamma emitting radionuclides is very portable. The radioactive source can be transported to remote locations, for example along pipelines, to perform radiography that would be extremely impracticable with X-ray sources.

Gamma radiation sources, such as $^{192}$Iridium and $^{60}$Cobalt, but also $^{75}$Selenium, $^{170}$Thulium and $^{169}$Ytterbium, are used to inspect a variety of materials. Gamma radiography concerns the testing and welds on piping, pressure vessels, storage containers, pipelines, and structures. Tested materials include steel and many other metals, but also concrete (locating rebar or conduit), and ceramics (used in the aerospace industry). Theoretically, industrial gamma radiography can be applied to any material, such as walls, ceilings, floors, square or rectangular containers or any hollow cylindrical or spherical object.

There are a number of safety considerations that are applied to the apparatus employing these radioactive sources. Additionally, certain safety devices and security features are specified for the device according to government and industry standards. Various entities have developed radiographic exposure containers/devices and radiographic systems which have, to some degree, satisfied appropriate safety attributes. Some of these devices and systems are discussed below.

Because the radiographic source is "always on", meaning that it is constantly and continually emitting radiation and cannot be "switched off" as an X-ray unit by removing the energizing power, it is necessary to provide shielding around the radiation source to provide radiation protection to the operators and the general public. Known techniques to accomplish this shielding are discussed below.

U.S. Pat. No. 4,220,864 to Sauerwein et al., which is incorporated herein by reference, describes a radiographic exposure container which has a "straight through" channel for manipulating the radiation source out of the exposure position into the working position, and then back again. Shielding is provided in all directions around the source outside the straight channel. Along the channel, in the "rearward" direction (i.e. the direction of attachment of the remote control), shielding is attached to the source assembly itself and moves with the source to the working position. In the forward direction, shielding is provided using a moveable shielded shutter which moves out of position to allow a through-channel to align with the source assembly and create a pathway toward the working position. At the conclusion of the radiographic exposure, after return of the source to the storage position, the shutter is closed, blocking the pathway and completing the shielding. The disadvantage of this approach is that a massive shutter must be manipulated and must have very precise dimensions to avoid gaps through which radiation could emerge in the "closed" position. This is also susceptible to being fouled by dirt and foreign matter during the normal course of use, which could prevent the shutter from closing properly and thereby failing to accomplish its intended purpose of shielding the emergent beam of radiation.

Another alternative of a "straight through" design is described in U.S. Pat. No. 4,211,928 to Parsons et al., which is incorporated herein by reference. This device also contains a shutter although this shutter is not a massive shielded shutter, but rather an implement used for signaling that the source assembly has returned to the shielded position within the device. Along the channel, in the rearward direction (i.e. the direction of attachment of the remote control), shielding is attached to the source assembly itself and moves with the source to the working position. The shielding in the forward direction is also provided by shielded elements that travel with the source assembly to the working position. Although this approach eliminates the need to manipulate a massive shield and its associated drawbacks, the disadvantage of this approach is that there are shielded elements both in front of and in back of the source which can interfere with the performance of the radiographic exposure.

An alternative to these "straight channel" shielded containers is described in U.S. Pat. No. 2,976,423 to Prest, which is incorporated herein by reference. This illustrates a "U" shaped channel surrounded by shielding, and a means for manipulating the radioactive source by means of a detachable cable. The "U" shaped channel is designed such that there are no direct paths for the radiation to emerge outside the body of the device. By bending the channel into the form of a "U", shielding is provided for the channel in all directions. This approach eliminates the necessity of moving a massive shielded shutter (as in Sauerwein et al. '864) and eliminates the necessity of the necessity of moving shielding material with the source (as in Munro et al. '928). However, the additional shielding necessary to compensate for the shielding missing from the "U" channel adds appreciably to the weight of the container. A similar arrangement is described in U.S. Pat. No. 3,147,383 to Prest, which is also incorporated herein by reference.

The coupling of the remote control, in its simplest form, is also described in U.S. Pat. No. 2,976,423 to Prest. In this arrangement, the remote control driving cable could be coupled to the radioactive source by merely driving the cable forward. The driving cable connector would enter the source connector, moving a spring which would then automatically latch the driving cable connector in position. A special tool may be required to decouple the connector elements.

An improved connector is described in U.S. Pat. No. 3,147,383 to Prest, which is incorporated herein by reference. In this case, the drive cable connector is manually joined to the source connector and is secured using a sleeve. Prest '383 also describes a means for securing the source in the shielded position within the storage container. This is accomplished by driving a pair of locking pins onto the cable of the source assembly cable which prevents the cable from moving. A disadvantage of this design was that it permits the locking pins to be engaged at any position along the driving cable as well, thereby locking the source in an exposing position.

An improvement to the above approach is described in U.S. Pat. No. 3,593,594 to Perry, which is incorporated herein by reference. Perry describes deficiencies of the prior art coupling devices. To address the described deficiencies, Perry provides for an apparatus for manipulating radioactive materials to and from a storage unit and more particularly, features in a coupling unit for coupling propulsion means for the source to the source and its storage unit. Perry provides for structures for rendering the coupler fail-safe to prevent coupling of the propulsion means with the storage unit unless a propelling cable and the source are properly connected; other structures are shown by Perry for preventing decoupling except when the source is in its storage unit and for facilitating connection of the propelling cable with the source.

The issue of coupling the operating control to the source assembly and exposure container is described in U.S. Pat. No. 5,065,033 to Parsons, which is incorporated herein by reference, and in which Parsons discusses U.S. Pat. No. 4,211,928 to Parsons et al. and U.S. Pat. No. 4,281,252 to Parsons et al., which are also incorporated herein by reference. Parsons '928 discloses a coupling apparatus which provides for automatic locking of the radioactive material within the storage unit when the control cable guides the radioactive material back to its stored position. Parsons '252 discloses coupling apparatuses which include the following fail safe features: (1) that the radioactive capsule remains in the storage unit until a proper connection has been made by the control cable assembly; (2) that the control cable assembly cannot be attached to the storage unit until the source cable assembly has been properly accessed by the control cable; (3) that the radioactive capsule must be safely stored in the storage unit before the control cable assembly can be disconnected. This arrangement does not, however, provide for the automatic locking of the radioactive capsule within the storage unit, upon its return to its stored position within the storage unit. Parsons '033 then discloses an improved coupling apparatus which includes disconnectable coupling devices having a connector assembly fixed to a storage unit in a radiographic system and a separable control cable assembly of tubular shape.

U.S. Pat. No. 5,418,379 to Parsons et al., which is incorporated herein by reference, describes improved control by added safety features to radiographic cameras. Among other features, Parsons '379 provides for a system that includes use of a plug assembly that cannot be completely removed until the opening at the plug assembly is shielded, and an interlock provided between the front and the back of the camera so that the control cables cannot be connected unless either the guide cable is connected or the plug assembly is in the front end.

Accordingly, it would be desirable to provide a system to overcome the manifest deficiencies in the current state of the art in connection with features and functions of radiation surveying and radiography equipment and to enhance radiation safety for the operator and the general public.

SUMMARY OF THE INVENTION

According to the system described herein, a radiography camera system includes an exposure container made from radiation shielding material and having a curved channel therein that terminates inside the exposure container, a first conduit portion having a first end coupled to the exposure container, a switch coupled to a second end the first conduit portion, a second conduit portion having a first end coupled to the switch, a guide tube coupled to the switch, a crank coupled to a second end of the second conduit portion, and a cable disposed in the crank and having a source assembly or a connector for a source assembly on an end thereof, the switch being actuated by the connector for the source assembly and/or a component of the source assembly to cause the cable to feed through the first conduit portion or the guide tube when the crank unwinds the cable. The exposure container may be made from depleted uranium, tungsten, and/or lead. The curved channel may be J-shaped. The switch may have a first opening that accepts the cable from the second conduit portion, a second opening coupled to the first conduit portion and a third opening coupled to the guide tube. Winding the cable through the second hole toward the crank may actuate the switch to cause the cable to feed through the third hole when the cable is unwound and winding the cable through the third hole toward the crank may actuate the switch to cause the cable to feed through the second hole when the cable is unwound. In response to tension from winding the cable, a portion of the switch may rotate to actuate the switch by feeding the cable through the second hole or the third hole. The radiography camera system may also include a ramp, proximal to a terminal end of the channel, that allows a portion of the source assembly to pass into the channel and prevents the portion of the source assembly from being removed from the channel and a push bar that manually engages the ramp to allow the portion of the source assembly to be removed from the channel. The radiography camera system may also include a pivot bar disposed inside the channel and having a hooked portion that engages a first portion of the source assembly when the source assembly is inserted into the channel to cause a second portion of the source assembly to pivot the pivot bar.

According further to the system described herein, a source assembly for a radiography camera includes a radioactive source, a connector that connects the source assembly to a cable of the radiography camera, a flexible cable coupled to the radioactive source and the connector, and a plurality of beads, disposed on the cable between the radioactive source and the connector, the beads providing radioactive shielding. The beads may be fixedly attached to the cable or may be strung loosely on the cable. The source assembly may also include a plurality of springs, disposed between the beads to maintain spacing therebetween. The source assembly may also include a first stop fixedly attached to the cable proximal to the radioactive source and a second stop fixedly attached to the cable proximal to the connector. The beads may be made depleted uranium, tungsten, and/or lead. The source assembly may be removeably attached to the cable.

According further to the system described herein, a coupling device includes an outer cylindrical portion having ramps thereon that engage with ramps on a boss attached to a container, an inner cylindrical portion disposed coaxially to and within the outer cylindrical portion, the inner cylindrical portion moving in an axial direction with respect to the outer cylindrical portion, tines on the inner cylindrical portion that engage with gaps in the boss, and a first cable connector disposed coaxially to and within the inner cylindrical portion, the first cable connector moving axially only when the coupling device is connected to the boss, where pushing the coupling device into the boss to engage the tines with the gaps and then rotating the outer cylindrical portion causes the first cable connector to be pressed against and connect with a second cable connector while the coupling device connects with the boss, the second source connector being coupled to the source and within the boss. Rotating the coupling device may cause the inner portion to move toward the boss to release the first cable connector. Moving the inner portion toward the boss may cause a locking bar to release the first cable connector to allow the cable to pass through the conduit and the container. The locking bar may have a flat portion that engages with the first cable connector to prevent axial movement thereof.

According further to the system described herein, an automatic securing mechanism for a radiography camera system has an exposure container made from radiation shielding material and has a curved channel therein that terminates inside the exposure container. The automatic securing mechanism includes a locking bar having at least one hole thereon with a first portion providing a relatively large opening when aligned with an opening of the channel and having a second portion providing a relatively small opening when aligned with the opening of the channel, an opening mechanism that causes the locking bar to move laterally with respect to the opening of the channel in a first direction to align the first portion of the hole with the opening of the channel when the securing mechanism is in an unlocked state, and a securing mechanism that causes the locking bar to move laterally with respect to the opening of the channel in a second direction to align the second portion of the hole with the opening of the channel when the securing mechanism is in a locked state. The automatic securing mechanism may also include a securing block, disposed between the locking bar and the exposure container, where the securing block moves in a direction perpendicular to the opening of the channel and a first spring, disposed between the securing block and the exposure container to urge the securing block toward the locking bar. The opening mechanism may include protrusions on the locking bar that engage with notches in the securing block to maintain the locking bar in a position that aligns the first portion of the hole with the opening of the channel. The securing mechanism may include a second spring that maintains the locking bar in a position that aligns the second portion of the hole with the opening of the channel. A portion of a source assembly may be larger than the first portion of the hole and moving the source assembly into the channel causes the securing block to be urged away from the locking bar to disengage the protrusions on the locking bar from the notches in the securing block. The automatic securing mechanism may also include a sled, coupled to the securing block and having an end portion proximal to a terminal end of the channel, where a source inserted into the channel engages the end portion of the sled to urge the securing block away from the locking bar to disengage the protrusions on the locking bar from the notches in the securing block.

According further to the system described herein, a crank moves a drive cable of a radiography camera system in forward direction and a reverse direction. The crank includes a control assembly housing, formed as a drum, a drive mechanism, disposed within a closed passageway of the control assembly housing, the drive mechanism and the control assembly forming a relatively small space for winding the cable about the control assembly, a crank arm attached to the drive mechanism, that slides within the closed passageway to wind and unwind the cable, and a handle attached to the crank arm. The crank arm may rotate about an axis that is in a plane containing the control assembly housing. The control assembly housing and the drive mechanism may inhibit winding and unwinding of the drive cable in response to the crank arm being in a same plane as the control assembly housing. The crank arm may be urged to being in the same plane as the control assembly housing and where an operator may move the crank arm for left-handed or right-handed turning of the crank. The drive cable may be relatively smooth.

According further to the system described herein, an exposure container for a radiography camera system includes a first portion made from radiation shielding material and containing a curved channel therein that terminates inside the exposure container and a second portion, separate from the first portion and made from radiation shielding material, where the second portion accommodates the first portion to form a shield that blocks radiation. The first portion may be made of tungsten. The second portion may be made of depleted uranium.

According further to the system described herein, a radiography system includes a conduit having a drive cable disposed therein, a crank coupled to a first end of the conduit, a switch coupled to an other end of the conduit, an exposure container having radiation shielding and having a bent channel therein. A bent portion of the bent channel terminates inside the shielding and an other end of the bent channel is coupled to one output of the switch. The radiography system also includes a guide tube coupled to an other output of the switch, where actuating the crank in a first direction causes a source assembly having a radioactive source to be pulled out of the exposure container and through the switch and where actuating the crank in a second direction opposite to the first direction causes the source assembly to be pushed back through the switch and into the guide tube. The source assembly may include a source capsule containing the radioactive source, a cable connector, and a flexible cable that couples the source capsule to the cable connector. The source assembly may also include at least one bead attached to the flexible cable between the source capsule and the cable connector. The radiography system may also include an automatic securing mechanism having a pivot bar disposed at least partially within the bent portion of the bent channel, where the pivot bar is in a first position when the source assembly is outside the bent channel and the pivot bar is in a second position when the source assembly is inside the bent channel and where, in the second position, an end of the pivot bar secures the at least one bead. The at least one bead may be made of tungsten. The radiography system may also include a ramp disposed within the bent portion of the bent channel, where the ramp allows the source capsule to enter the bent channel but prevents the source capsule from being pulled out of the bent channel. The radiography system may also include a push rod, coupled to the exposure container, that guides the source capsule past the ramp when the source capsule is being pulled out of the bent channel. The control adaptor may be coupled to the exposure container using a connector that simultaneously connects the control adaptor to the exposure container and connects the source assembly to the drive cable. The drive cable used in connection with actuating the crank in the first direction may be used in connection with actuating the crank in the second direction. After the source assembly has been pushed into the guide tube, actuating the crank in the first direction may cause the source assembly to be pulled out of the guide tube and through the switch and actuating the crank in the second direction opposite to the first direction may cause the source assembly to be pushed back through the switch and into the exposure container.

According to the system described herein, operating a radiography system includes providing a conduit having a drive cable disposed therein, a crank coupled to a first end of the conduit, and a switch coupled to an other end of the conduit, connecting, to one output of the switch, an exposure container having radiation shielding and having a bent channel therein, where a bent portion of the bent channel terminates inside the shielding and an other end of the bent channel is coupled to the one output of the switch, connecting a guide tube to an other output of the switch, actuating the crank in a first direction to cause a source assembly having a radioactive source to be pulled out of the exposure container and through the switch, and actuating the crank in a second direction opposite to the first direction to cause the source assembly to be pushed back through the switch and into the guide tube. The source assembly may include a source capsule containing the radioactive source, a cable connector, and a flexible cable that couples the source capsule to the cable connector. The source assembly may include at least one bead attached to the flexible cable between the source capsule and the cable connector. An automatic securing mechanism may include a pivot bar disposed at least partially within the bent portion of the bent channel, the pivot bar being in a first position when the source assembly is outside the bent channel and the pivot bar being in a second position when the source assembly is inside the bent channel, where, in the second position, an end of the pivot bar secures the at least one bead. The at least one bead may be made of tungsten. A ramp disposed within the bent portion of the bent channel may allow the source capsule to enter the bent channel but prevent the source capsule from being pulled out of the bent channel. A push rod, coupled to the exposure container, may guide the source capsule past the ramp when the source capsule is being pulled out of the bent channel. The switch may be coupled to the exposure container using a connector that simultaneously connects the switch to the exposure container and connects the source assembly to the drive cable. The drive cable used in connection with actuating the crank in the first direction may be used in connection with actuating the crank in the second direction. Operating a radiography system may also include, after the source assembly has been pushed into the guide tube, actuating the crank in the first direction to cause the source assembly to be pulled out of the guide tube and through the switch and actuating the crank in the second direction opposite to the first direction to cause the source assembly to be pushed back through the switch and into the exposure container.

According further to the system described herein, an exposure container that maintains a radioactive source includes radiation shielding that inhibits transmission of radiation and a bent channel in the radiation shielding, where a bent portion of the bent channel terminates inside the radiation shielding and an other end of the bent channel provides an opening in the radiation shielding for inserting the radioactive source. The bent channel may be in a shape of a J.

According further to the system described herein, a crank system for moving a an object attached to a cable includes a hooped-shaped control assembly housing having a closed passageway therein, a drive mechanism disposed within the passageway for winding the cable thereon, and a handle assembly, attached to the drive mechanism at an attachment point to project to an inward portion of the control assembly and having a crank arm that is rotatable about the attachment point. Rotating the crank handle about the attachment point to a predetermined position engages the crank arm with a slot in the housing to inhibit movement of the drive mechanism within the passageway. The handle assembly may be rotatable to either side of the control assembly to facilitate switching between right hand and left hand use without reorienting the crank system. The predetermined position may correspond to an axis of the crank arm pointing to a center of the control assembly to urge the drive mechanism toward the inside surface of the passageway to inhibit movement of the drive mechanism within the passageway. The handle assembly may include a handle rotatably mounted on the crank arm. The object may be a radioactive source.

According further to the system described herein, a radioactive source assembly includes a radioactive source provided in a source capsule, a cable connector that provide a connection of the source assembly to a drive cable, a plurality of shielding components, and a flexible cable that couples the source capsule to the cable connector, where the shielding components are strung on and attached to the flexible cable. At least some of the shielding components may be beads. At least some of the shielding components may be made of tungsten or a different heavy alloy or combination of heavy alloys and/or tungsten.

According further to the system described herein, a connection system includes a first connector on a drive cable of a radiography system, a second connector on a source assembly of a radiography system, a third connector on a switch of a radiography system, where the switch includes the drive cable, and a fourth connector on an exposure container of a radiography system that includes the source assembly, where the first and second connectors are coupled at the same time as the third and fourth connectors when the switch is attached to the exposure container.

The system described herein includes any method of making or using (operating) the components described herein.

Channels in an exposure container with a J-shaped or straight-thru internal source path tube are essentially immune to excessive source path tube wear. Although several straight-thru designs exist, current straight-thru devices utilize either one of two alternate design features that are each undesirable. The first undesirable option is that the source assembly must have shielding, such as articulating tungsten slugs, attached to a front end (opposite a connector end) of the source assembly (with a sealed radioactive capsule located in the middle) to prevent radiation from being emitted out the front of the shielded device when the source assembly is fully seated therein. The disadvantage of a source assembly with shielding attached to a front end is that, because the sealed capsule is located in the middle of the source assembly, the sealed capsule is unable to reach a tip end of a hollow guide tube into which the source assembly is cranked to emit radiation. In some applications, an inability to position the radioactive source capsule at the tip end of the guide tube limits the versatility of the system. An alternate the first undesirable feature is to eliminate shields attached to the source assembly in front of the sealed radioactive capsule and, instead, utilize a movable shield (i.e., shutter) at the front of the exposure container to provide radiation shielding when the source assembly is fully seated within the device. The disadvantage of this type of device is that it increases the number of moving parts which are subject to malfunctions. The system described herein utilizes a source assembly that (a) does not have radiation shielding attached to a front end of the source assembly, and (b) does not utilize a movable shield at the front of the exposure container, yet the internal source path (J-tube) essentially never wears out.

In addition, existing systems crank a source assembly forward, out of an exposure container, and into a hollow guide tube. In contrast, the system described herein cranks the source assembly backwards, into a switch, and then forward into a hollow guide tube. The switch allows the adoption of a device design and a source assembly design that does not have undesirable features such as a shielded device shutter or source assembly shields in front of the radioactive source capsule.

The source assembly shields of the system described herein do not connect components of the source assembly together. In existing shielded source assembly designs, a connector is attached to one or more shields, such as articulating tungsten slugs, the end of which is connected to a sealed radioactive capsule, which may be attached to additional shields in front. In the system described herein, a flexible cable is attached to a connector at one end and to a source capsule at the other. The shields may be beads with internal thru-holes that allow the beads to be fitted over the cable during assembly and are held in position by various mechanical mechanisms, such as springs between the beads. Unlike existing shielded source assembly designs, if a shield breaks in the system described herein, it does not cause loss of the radioactive sealed source capsule.

The system described herein also provides a shielded device (radiography camera) and control assembly connector system that simultaneously connects, in one operation, a drive cable to a source assembly, and connects the control assembly to the shielded device. This provides two benefits: First, it is fast; the entire connection operation is completed within two seconds. Existing designs require first connecting the drive cable to the source assembly and then connecting the control assembly to the device, which requires significantly more time. Second, the system described herein is simple; the drive cable to source assembly connection does not require manual manipulation of small connector components (i.e., internal piston and spring) which can be difficult to performed while wearing heavy gloves. For a conventional system, in very cold climates, the worker must remove one or both insulated gloves to make a connection, which is not necessary for the system described herein.

The automatic securing mechanism (ASM) of the system described herein automatically secures (captures) a source assembly when the source assembly is cranked into, and fully seated within, a shielded exposure container. The ASM of the system described herein is triggered by movement of a sealed source capsule portion of the source assembly as the capsule portion is cranked into a fully seated position within the exposure container. In contrast, existing designs are triggered by movement of other components of the source assembly (i.e., locking ball, connector, etc.). The result is that existing designs may trigger (engage) the ASM even if the sealed radioactive capsule has broken off the source assembly. In contrast, If the capsule has broken off the source assembly for the system described herein, the ASM will not be triggered.

The system described herein automatically prevents the drive cable from inadvertent movement by urging the crank arm to a position that inhibits movement, thereby preventing source assembly movement, when the cranking handle is released by a worker. To operate the control assembly, the worker manually moves (rotates) the crank handle into an operating position. When released, an internal force, such as a spring, automatically urges (rotates) the crank arm into a default locked position. Also, the crank arm and crank handle allow a right or left handed worker to operate the control assembly without the necessity of relocating the crank handle or inverting the cranking assembly upside down.

The drive cable used for the system described herein is not driven in a conventional manner. Existing drive cables employ an outer helical wrapping of small diameter cable that engages a corresponding gear inside the cranking mechanism. The system described herein uses a drive cable design that does not need an outer wrap to engage with a drive gear so that the drive cable is relatively smooth.

BRIEF DESCRIPTION OF THE DRAWINGS

Embodiments of the system described herein will be explained in more detail below on the basis of the figures, which are briefly described as follows.

DETAILED DESCRIPTION OF VARIOUS EMBODIMENTS

The system described herein may include radiation emitting units or equipment, for example, used for industrial radiography (e.g., non-destructive testing) and/or for medical purposes such as brachytherapy devices. In an embodiment, the radiation emitting unit may include an exposure container, for example, provided as a depleted uranium (DU) shielded, ANSI Category II ("crank-out") exposure container, see for example, ANSI N43.9 and ISO 3999. The system described herein may be used in connection with the application of gamma-emitting radiation sources, such as sources containing $^{192}$Iridium, $^{60}$Cobalt, $^{75}$Selenium, $^{170}$Thulium and/or $^{169}$Ytterbium as the gamma radiation-emitting source and to methods of delivering these sources for temporary application. For discussions of gamma-emitting radiation sources that may be used in connection with the system described herein, reference is made to U.S. Pat. No. 8,357,316 B2 to Munro et al. entitled "Gamma Radiation Source" and to US Publication No. 2013/0009120 A1 to Munro et al. entitled "Radioactive Material Having Altered Isotropic Composition," which are incorporated herein by reference. Note that other types of sources, such as neutron sources provided for neutron radiography, may be used with the system described herein.

The system described herein uses an exposure container having a J-shaped channel (J-channel) that may significantly reduce wear to the source tunnel to significantly extend the useful life of the exposure container and reduce the travel length of drive cable passing through the source tunnel in a Category II device. The drive cable may be aircraft cable that is relatively smooth (i.e., does not use an outer helical wire attached to and wrapped around the drive cable because there is no small diameter gear that engages the cable). The friction from drive cable passing through a source tunnel creates significant wear, so that shorter cable travel length may substantially reduce the wear and extend the life of the device. The channel inside the exposure container does not necessarily need to have a J-shape, but may be bent in other shapes. Generally, a bent portion of the bent channel terminates inside the shielding of the exposure container.

Figure 1:
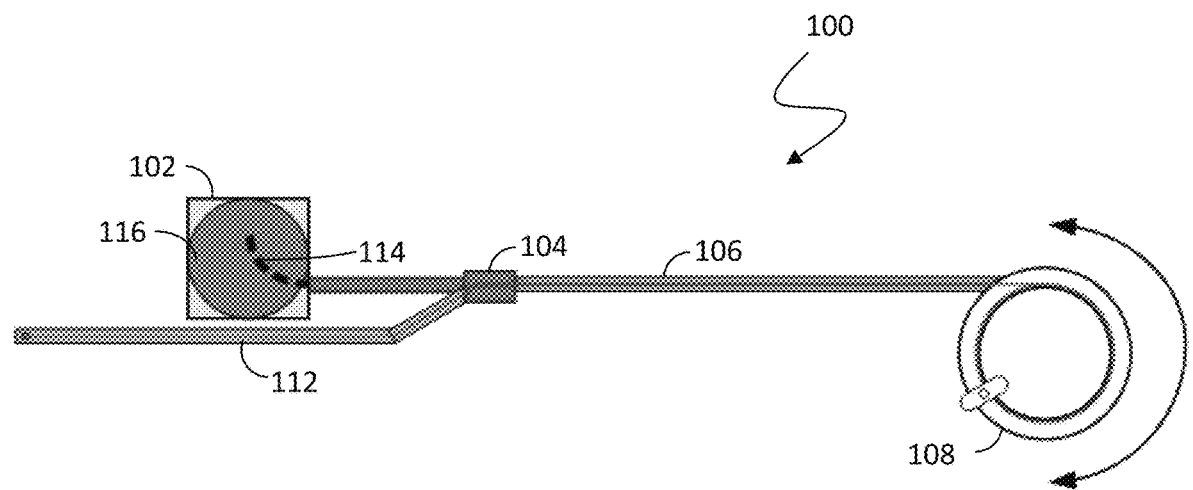
FIG. 1 is a schematic illustration of a system having an exposure container, a switch, a conduit, a crank, and a guide channel according to an embodiment of the system described herein.

Referring to FIG. 1, a radiography camera system 100 is shown as having an exposure container 102 coupled to a switch 104 (via a conduit therebetween), which is coupled to a conduit 106 that may be used for housing a drive cable (not shown in FIG. 1) that moves back and forth in the conduit 106 in response to rotation of a crank 108, which is coupled to the conduit 106. The switch 104 may also be coupled to a guide tube 112. In some embodiments, the switch 104 may be coupled directly to the exposure container 102 without any conduit therebetween. Coupling to the exposure container 102 may be provided by a control adaptor assembly (not shown in FIG. 1), which is described in more detail elsewhere herein.

The exposure container 102 includes a J-channel 114 provided in shielding 116, which may be made from depleted uranium, but may be made from any other suitable material, consistent with the discussion herein, such as tungsten or lead shielding material or any other dense material that may be used for radiation shielding, such as materials having a density greater than 6 g/cm$^3$. In some cases, other types of shielding for other types of radiation may be used. For instance, other types of radiation may be shielded with thin metal or plastic. The J-channel 114 terminates inside the exposure container 102 and is curved so that when a radiation source (not shown in FIG. 1) is disposed at a terminal end of the J-channel 114, radiation from the source does not emanate from the opening of the J-channel 114.

Operation of the radiography camera system 100, which is described in more detail elsewhere herein, includes rotating the crank 108 in a first direction (winding) to manipulate a source assembly (not shown in FIG. 1) attached to the drive cable to cause the source assembly to travel out of the exposure container 102 and into the switch 104, which actuates so that rotating the crank 108 in an other direction (unwinding) moves the source assembly from the switch 104 into the guide tube 112 to be deployed to perform radiography on a component (not shown) such as a pipe. The component on which radiography is to be performed is attached to the guide tube 112 on an end opposite to an other end of the guide tube 112 that is attached to the switch 104. After deployment, the crank 108 is rotated to cause the source assembly to reenter the switch 104, which actuates to allow the crank 108 to move the source assembly from the switch 104 back into the exposure container 102. The crank 108 may be turned manually or using a motor (or similar) that may be actuated directly by an operator or may be processor controlled at least to some extent.

The switch 104 may use conventional mechanical components to automatically change state to allow the source to be switched between the two different paths. Such switching mechanisms are well known to those skilled in the art. See, for example, U.S. Pat. No. 2,295,358 to Schaffan or U.S. Pat. No. 2,772,843 to Rexford, both of which are incorporated by reference herein. The mechanical components may cause the source to be pushed down one of the paths after the source has been pulled through another one of the paths.

In an embodiment herein, the switch 104 may be connected and disconnected from the exposure container 102 and the conduit 106 (and possibly also the guide tube 112) to facilitate taking the system 100 apart for storage/transport. In other embodiments, the switch 104 may be permanently attached to, and be part of, the conduit 106. As discussed in more detail elsewhere herein, the system 100 may provide for rapid and relatively straight-forward assembly.

Figure 2A:
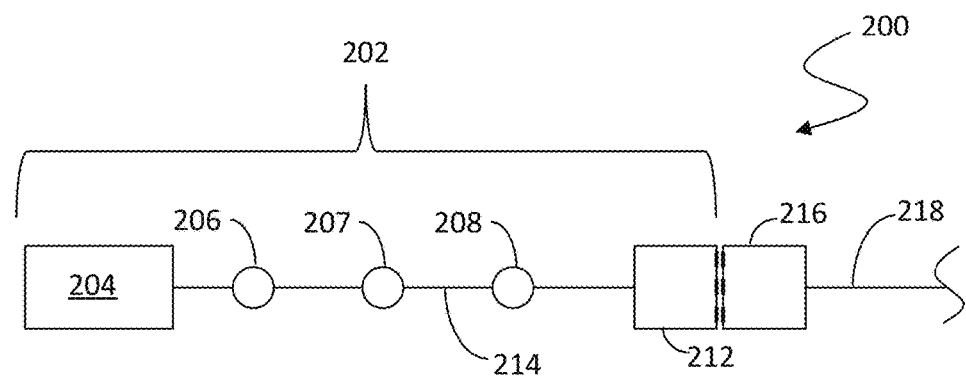
FIGS. 2A-2D are schematic illustrations of source assemblies according to different embodiments of the system described herein.

Referring to FIG. 2A, an embodiment 200 of a source assembly 202 includes a source capsule 204, a plurality of beads 206-208, and a connector 212. The beads 206-208 may be made out of tungsten or some other suitable material. The source capsule 204 is a sealed container containing a gamma-emitting source material, such as gamma-emitting radiation sources, such as sources containing $^{192}$Iridium, $^{60}$Cobalt, $^{75}$Selenium, $^{170}$Thulium and/or $^{169}$Ytterbium. Of course, other possible gamma-emitting sources may be used. The source capsule 204 may be attached to a flexible cable 214 to which the beads 206-208 and the connector 212 are also attached. In an embodiment herein, the flexible cable 214 may be type 316SS aircraft cable, although of course other types of cable may be used. Attaching the beads 206-208 to the flexible cable 214 reduces the possibility of a disconnect due to fractured tungsten (or similar) parts that are only attached to a cable at each end of the parts. As described in more detail elsewhere herein, the source assembly 202 is moved out of the exposure container 202, the switch 104 and the guide tube 112.

The connector 212 mates with a similar connector 216 provided at an end of a drive cable 218, which travels back and forth in the conduit 106, described above. In an embodiment herein, an end of the source assembly 202 that includes the source capsule 204 enters the J-channel 114 of the exposure container 102 first, followed by the beads 206-208. The beads 206-208 may be the same diameter (or nearly the same diameter) as the J-channel 114 and may provide radiation shielding to minimize radiation emitted by the exposure container 102 when the source capsule 204 is at or near a terminal end of the J-channel 114. In an embodiment herein, the connector 212 never enters the J-channel 114 but, instead, the flexible cable 214 is long enough to allow the connector 212 to be presented outside the exposure container 102 for connection of the drive cable 218 when the end of the source capsule 204 is at or near a terminal end of the J-channel 114. Generally, the flexible cable 214 is long enough to allow the connector 212 to be presented outside the exposure container 102 for connection to the drive cable 218 (which is fed through the switch 104) when the end of the source capsule 204 is at or near a terminal end of the J-channel 114. In an embodiment herein, the connector 212 never enters the J-channel 114 but, instead, the flexible cable 214 is long enough to allow the connector 212 to be presented outside the exposure container 102 for connection of the connector 216 (which is fed through the switch 104) when the switch 104 is connected to the exposure device 102 and the end of the source capsule 204 is at or near a terminal end of the J-channel 114.

In an embodiment herein, the crank 108 may include a large diameter drum that propels the drive cable 218 forward and stores the drive cable 218 when cranked back in. This may be advantageous over existing control assembly designs in which additional conduit is needed for storing the drive cable and the drive cable is propelled by the movement of a small diameter gear that engages an outer helical wire attached to and wrapped around the drive cable. The drive cable 218 does not need an outer helical wire. In an embodiment herein, the conduit 106 may not need an outer coating and thus may exhibit reduced weight. The crank 108 may be equally ergonomic to right and left hand users. The crank 108 may be equipped with a feature that automatically secures the drive cable 218 from movement when the user releases the crank 108, for example, similar to a dead man break. The drive cable 218 may be a stainless steel drive cable that does not have a large outer helix wire to engage with a gear.

Figure 2B:
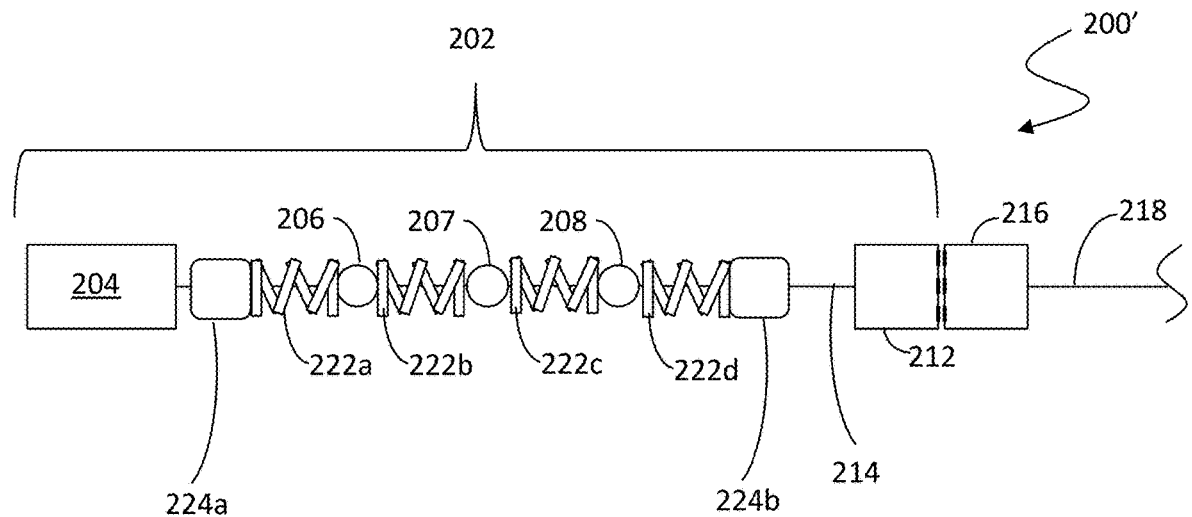

Referring to FIG. 2B, an alternative embodiment 200' of the source assembly 202 includes the source capsule 204, the plurality of beads 206-208, and the connector 212. However, for the alternative embodiment 200', the beads 206-208 are not attached to the cable 214. Instead, the beads 206-208 are loosely strung on the cable 214 and are maintained in position on the cable 214 by springs 222a-222d. The springs 222a-222d may be made out of stainless steel or some other suitable material. Of course, other types of spacers could be used instead of the springs 222a-222d. The beads 206-208 and the springs 222a-222d alternate on the cable 214 and are placed between a first stop 224a and a second stop 224b. Just as with the beads 206-208, the springs 222a-222d may provide radiation shielding to minimize radiation emitted by the exposure container 102 when the source capsule 204 is at or near a terminal end of the J-channel 114. The stops 224a, 224b may be attached to the cable 214.

Figure 2C:
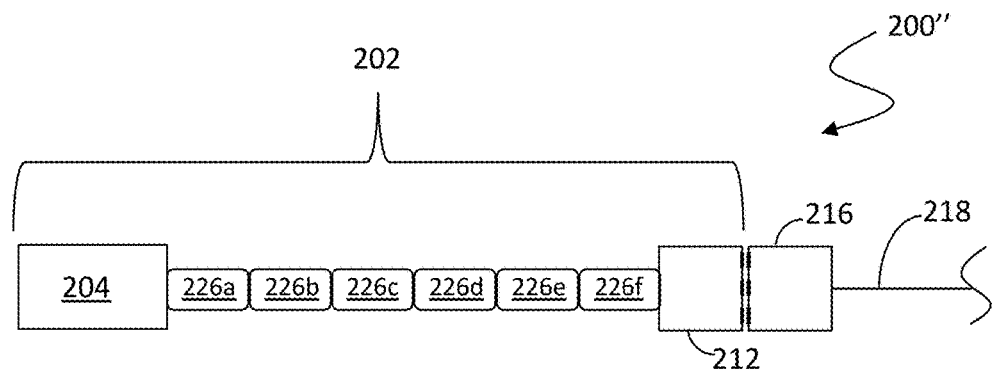

Referring to FIG. 2C, an alternative embodiment 200" of the source assembly 202 includes the source capsule 204 and the connector 212 that are coupled by a plurality of links 226a-226f. The alternative embodiment 200" does not use a cable, beads, or stops. Instead, the links 226a-226f are relatively stiff and may be attached together by a pin between each pair of the links 226a-226f. Each attachment from a first one of the links 226a-226f to a second one of the links 226a-226f allows the second one of the links 226a-226f to swivel in one plane. In an embodiment herein, each pair of the links 226a-226f swivels on a plane that is offset ninety degrees with respect to a swivel plane of adjacent pairs of the links 226a-226f. Just as with the beads 206-208 and the springs 222a-222d, the links 226a-226e may provide radiation shielding to minimize radiation emitted by the exposure container 102 when the source capsule 204 is at or near a terminal end of the J-channel 114.

Figure 2D:
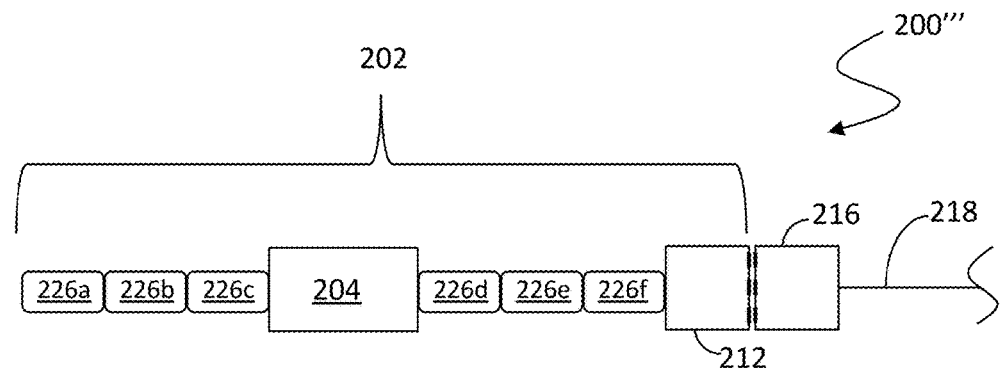

Referring to FIG. 2D, an alternative embodiment 200''' of the source assembly 202 includes the source capsule 204 and the connector 212 and the links 226a-226f. The alternative embodiment 200''' is like the embodiment 200" of FIG. 2C, except that the embodiment 200''' is suitable for systems where an exposure container contains a passage for the source capsule 204 that passes all the way through the exposure container (i.e., there is no terminal end of the passage like the J-channel 114 illustrated herein). The links 226a-226c provide shielding on one side of the source capsule 204 and the links 226d-226f provide shielding on an other side of the source capsule 204. In an embodiment herein, the source assembly 202 may be provided as described in U.S. Pat. No. 8,998,488 to Christopher Cole titled "RADIOGRAPHIC PROJECTOR", which is incorporated by reference herein.

In some embodiments, the source 204 may be detachable. For example, the source 204 shown in FIG. 2A or FIG. 2B may be removeably attached to the cable 214 using any appropriate mechanism of removable attachment, including conventional mechanisms such as a clip. It is also possible for the source 204 to be removebly attached in the embodiments illustrated in FIGS. 2C and 2D using, for example, pin(s) to attach the source 204 to adjacent ones of the links 226a-226f. Note also that, in some cases, a source and/or shield(s), etc. may be integrated with the cable and thus no source assembly is provided. For example, one or more shields and a source (or multiple sources) may be attached to the cable so that no source assembly is provided.

Figure 3:
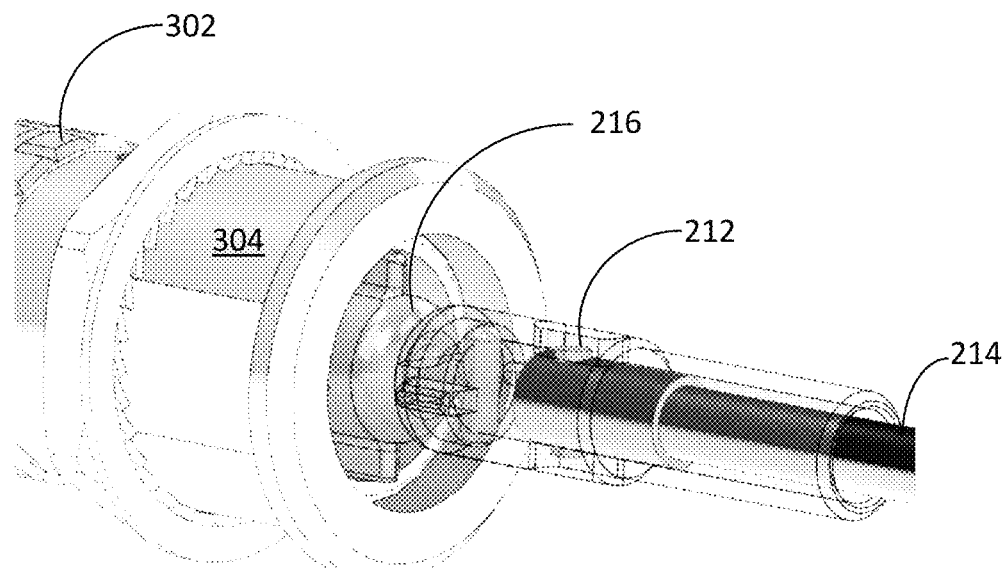
FIG. 3 is a schematic illustration of a connector for a conduit and cables according to an embodiment of the system described herein.

Referring to FIG. 3, a connector 302 is shown as including the connector 216 that is used to connect the drive cable 218 (not shown in FIG. 3) to the source assembly 202. The connector 302 is provided at an end of the switch 104 and couples to a corresponding connector 304 provided on the exposure container 102 (not shown in FIG. 3). In an embodiment herein, the connector 216 couples to the connector 212 at the end of the flexible cable 214 for the source assembly 202 by having a male-shaped cable connection on the connector 212 be inserted into a female-shaped receptacle on the connector 216, but of course other types of cable connections are possible. In an embodiment herein, the switch 104 is connected to the exposure container 102 at the same time that the drive cable 218 is connected to the source assembly 202. This may be accomplished in a single, one-handed pushing/twisting motion.

Figure 4:
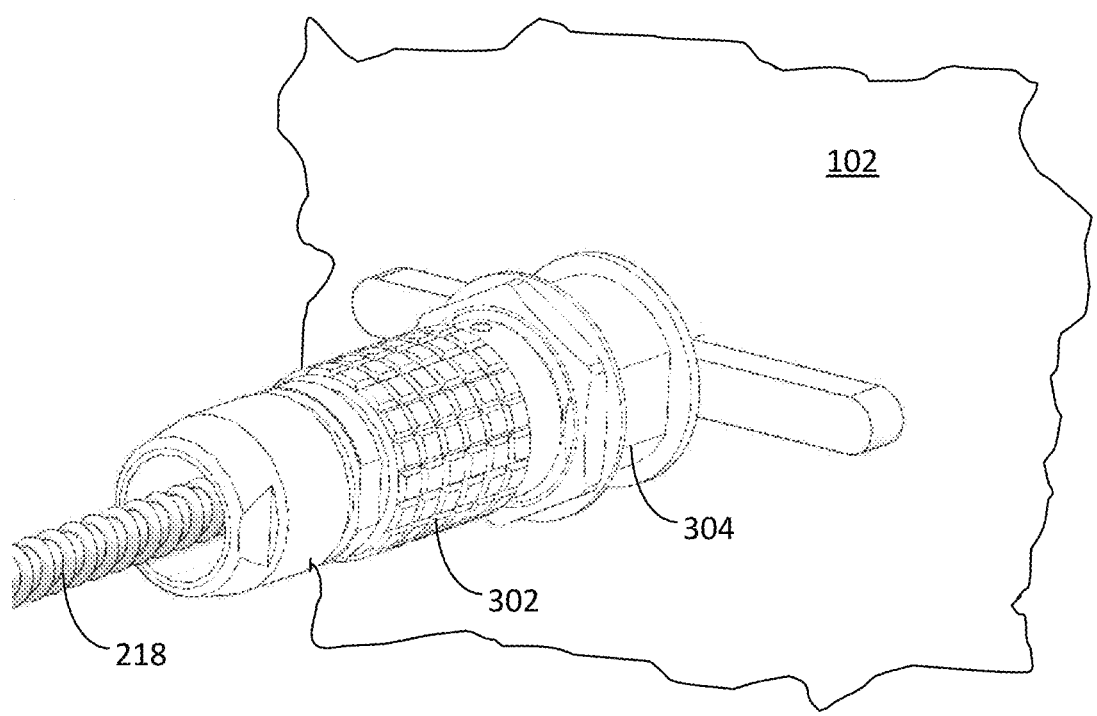
FIG. 4 is a schematic illustration of connection a conduit and a switch according to an embodiment of the system described herein.

Referring to FIG. 4, the connectors 302, 304 are shown without the conduit 106 or the switch 104 to reveal the drive cable 218. The connector 304 is shown as being attached to the exposure container 102. In an embodiment herein, the connectors 302, 304 may be disconnected using a conventional "quick release" mechanism while, at the same time the cable connectors 212, 216 may be disconnected using a twisting motion. Thus, it is possible for an operator to connect and disconnect the switch 104 to the exposure container 102 with one hand. In an embodiment herein, the crank 108 may be connected to the conduit 106 in a similar fashion along with separate portions of the drive cable 218 provided with each of the conduit 106 and the crank 108.

Figure 5A:
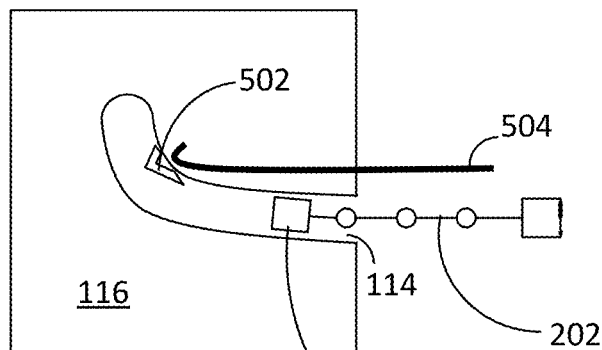
FIGS. 5A-5C illustrate an automatic securing mechanism according to an embodiment of the system described herein.
Figure 5B:
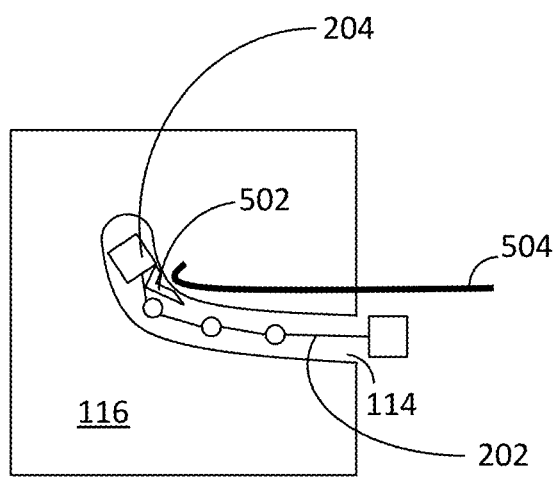
Figure 5C:
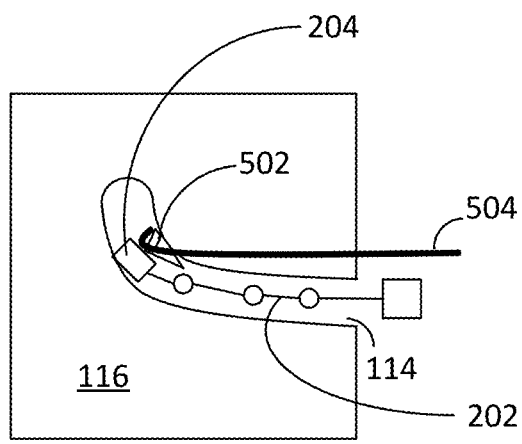

Referring to FIG. 5A, the J-channel 114 and the shielding 116 are shown with the source assembly 202 partially inserted into the J-channel 114 in connection with a first embodiment of an automatic securing mechanism. The J-channel 114 includes a ramp 502 that is used to secure the source assembly by securing the source capsule 204 when the source assembly 202 is inserted sufficiently into the J-channel 114. The ramp 502 allows the source capsule 204 to pass as the source capsule 204 is being pushed by the drive cable 218 toward the terminal end of the J-channel 114. FIG. 5B shows the source assembly 202 in a locked position where the ramp 502 prevents the source capsule 204 from moving away from the terminal end of the J-channel. In an embodiment herein, an operator may confirm that the source capsule 204 is in a locked position by attempting to gently crank the source capsule 204 out of the J-channel 114. FIG. 5C illustrates an operator releases the source assembly 202 from the J-channel by actuating a push rod 504, which pushes on the source capsule 204 away from the ramp 502 to allow the source capsule 204 to clear the ramp 502 as the source assembly is withdrawn from the J-channel 114. In some embodiments, the push rod 504 is actuated to lock the source capsule 204 into the J-channel 114 in response to the source capsule 205 being inserted into the J-channel 114 and passing the ramp 502.

Figure 6A:
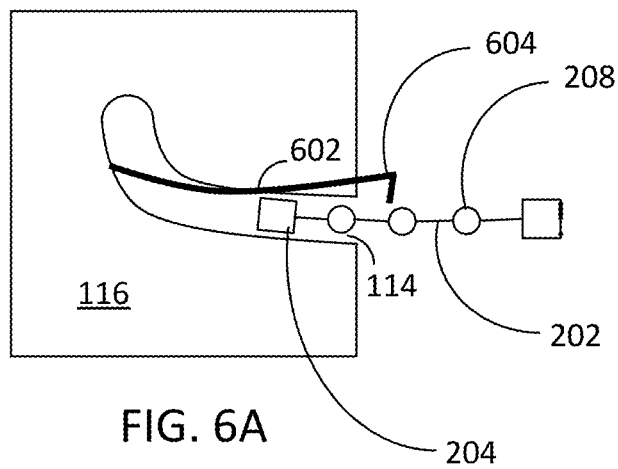
FIGS. 6A-6C illustrate an automatic securing mechanism according to an alternative embodiment of the system described herein.
Figure 6B:
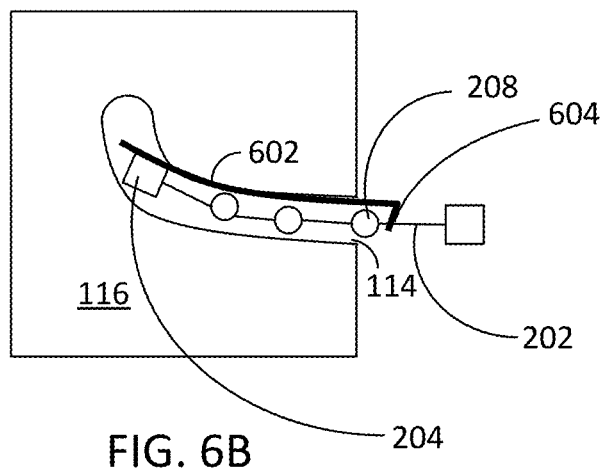
Figure 6C:
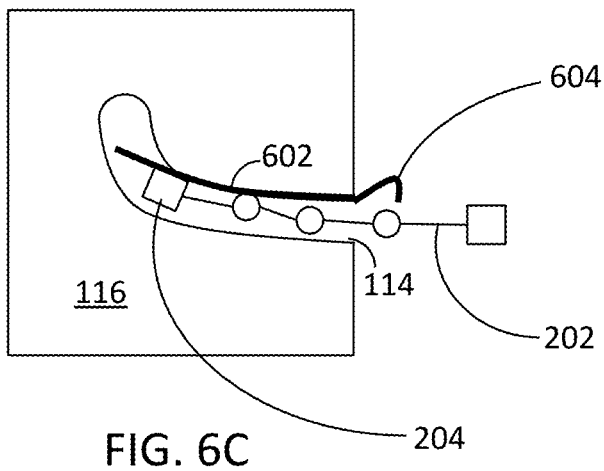

Referring to FIG. 6A the J-channel 114 and the shielding 116 are shown with the source assembly 202 partially inserted into the J-channel 114 in connection with a second embodiment of an automatic securing mechanism. In this embodiment, there is no ramp. Instead, the J-channel 114 includes a pivot bar 602 that is used to secure the source assembly by securing the bead 208 when the source assembly 202 is inserted sufficiently into the J-channel 114. The pivot bar 602 pivots from a first position shown in FIG. 6A to a second position shown in FIG. 6B as the source assembly 202 is being pushed by the drive cable 218 toward the terminal end of the J-channel 114. FIG. 6B shows the source assembly 202 in a locked position where the pivot bar 602 secures the bead 208 to prevent the source assembly 202 from moving away from the terminal end of the J-channel. The pivot bar 602 includes a hooked end portion 604 that retains the bead 208. As with the embodiment discussed above, an operator may confirm that the source capsule 204 is in a locked position by attempting to gently crank the source capsule 204 out of the J-channel 114. Note, however, that the embodiment of FIG. 6B also provides the operator with visual indication that the source capsule 204 is in a locked position by observing the hooked portion 604 and the bead 208. FIG. 6C illustrates an operator releases the source assembly 202 from the J-channel by lifting the hooked portion 604 of the pivot bar 602 to allow the bead 208 (and other components of the source assembly 202) to exit from the J-channel 114.

Figure 7:
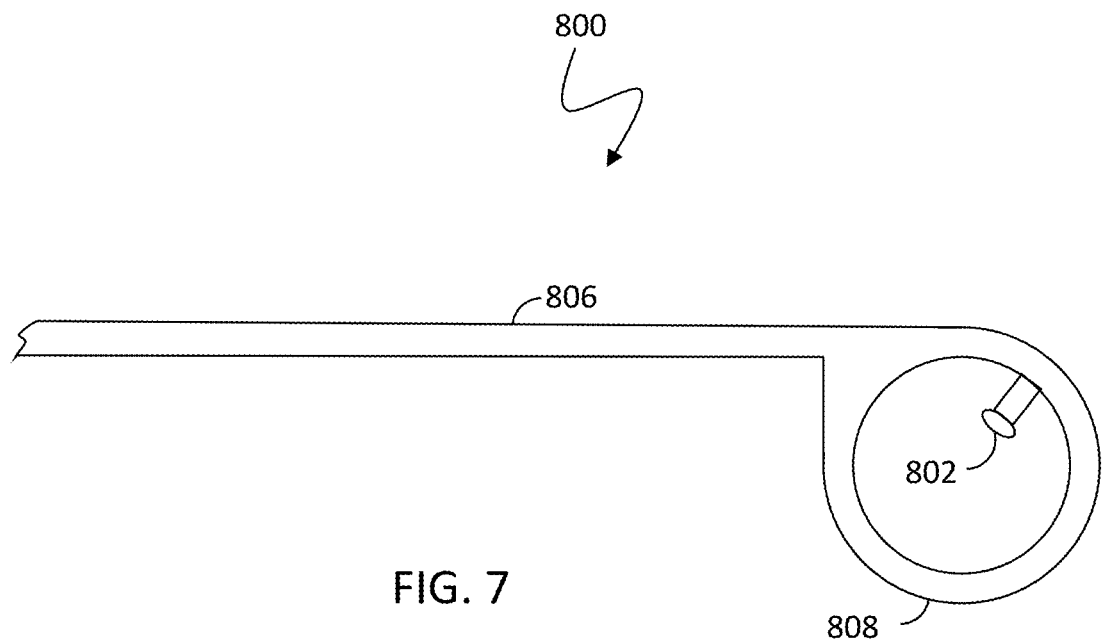
FIG. 7 is a schematic illustration of crank system having control assembly housing, a handle system and a conduit according to an embodiment of the system described herein.

Referring to FIG. 7, a crank system 800 includes a handle system 802, a conduit 806, and a control assembly 808. The handle system 802 facilitates winding the cable (not shown in FIG. 7) in a forward direction and a backward direction, as described elsewhere herein. The handle system 802 can restrict motion of the cable by holding the cable firmly in one position. In addition, the handle system 802 provides a reversible handle that can be used with a right hand or left hand without needing to re-orient the crank system 800. The conduit 806 is similar to the conduit 106 of FIG. 1, described above, and provides protection for a cable that slides therein. The control assembly 808 may be hoop-shaped (generally hollow in an inward portion), except for the handle assembly 802 that projects to the inward portion of the control assembly 808. Projecting the handle assembly 802 to an inward portion of the control assembly 808 facilitates reversing the handle assembly 802 for right and left handed operators, as described in more detail elsewhere herein.

Figure 8:
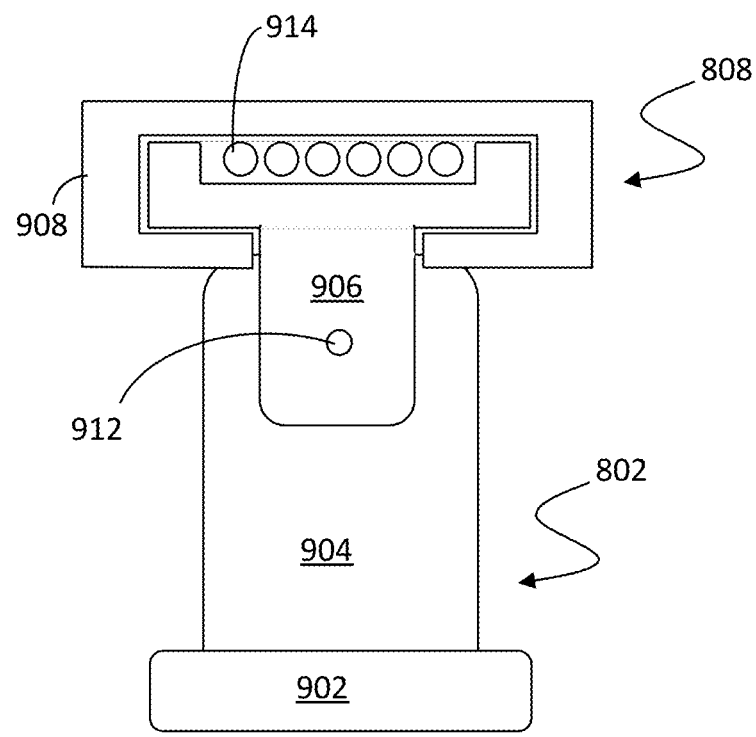
FIG. 8 is a schematic illustration showing a handle system according to an embodiment of the system described herein.

Referring to FIG. 8, a cutaway cross-section of the control assembly 808 is shown with the handle assembly 802. The handle assembly 802 includes a handle 902 and a crank arm 904. Use of the handle 902 and the crank arm 904 is described in more detail elsewhere herein. The control assembly 808 includes a drive mechanism 906 that is disposed inside a closed passageway within a control assembly housing 908 that is in a shape of a drum. The drive mechanism 906 slides within the housing 908 in a direction that is perpendicular to the view shown in FIG. 8. Since the control assembly 808 is circular, the drive mechanism slides within the control assembly housing 908 along the circular shape of the control assembly 808. The crank arm 904 is attached to the drive mechanism 906 by a pin 912 that allows the crank arm 904 to rotate about an axis that is perpendicular to the view shown in FIG. 8 (i.e., an axis in a plane containing the control assembly 808), as described in more detail elsewhere herein. A drive cable 914 that is attached to a radioactive source (not shown in FIG. 8) is wound around the control assembly housing 908. The handle assembly 802 is used to move the drive mechanism within the control assembly housing 908 to wind and unwind the drive cable 914 to cause the radioactive source to traverse the conduit 806, as described elsewhere herein. The drive cable 914 may be relatively smooth (i.e., does not use an outer helical wire attached to and wrapped around the cable 914 because there is no need to use q small diameter gear to engage the cable 914).

In some circumstances, it is desirable to inhibit movement of the cable 914. For example, when the radioactive source is deployed, it may be desirable to prevent the source from being inadvertently moved. In such a case, the crank arm 904 and the housing 908 cooperate to provide a brake to inhibit movement of the drive mechanism 906 within the control assembly housing 908, and thus prevent inadvertent and undesirable movement of the cable 914. In the position shown in FIG. 8, with an axis of the crank arm 904 pointing to a center of the control assembly 808 (i.e., the crank arm 904 and the control assembly 808 are essentially in a same plane), a portion of the crank arm 904 slides into a slot (not shown in FIG. 8) that inhibits movement of the crank arm 904 and the drive assembly 906 that is attached thereto. In other embodiments, it is possible to have the crank arm 904 urge the drive assembly 906 toward inside surfaces of the control assembly housing 908 so that frictional forces between the crank arm 904 and the drive assembly 906 inhibit movement of the drive assembly 906.

Figure 9A:
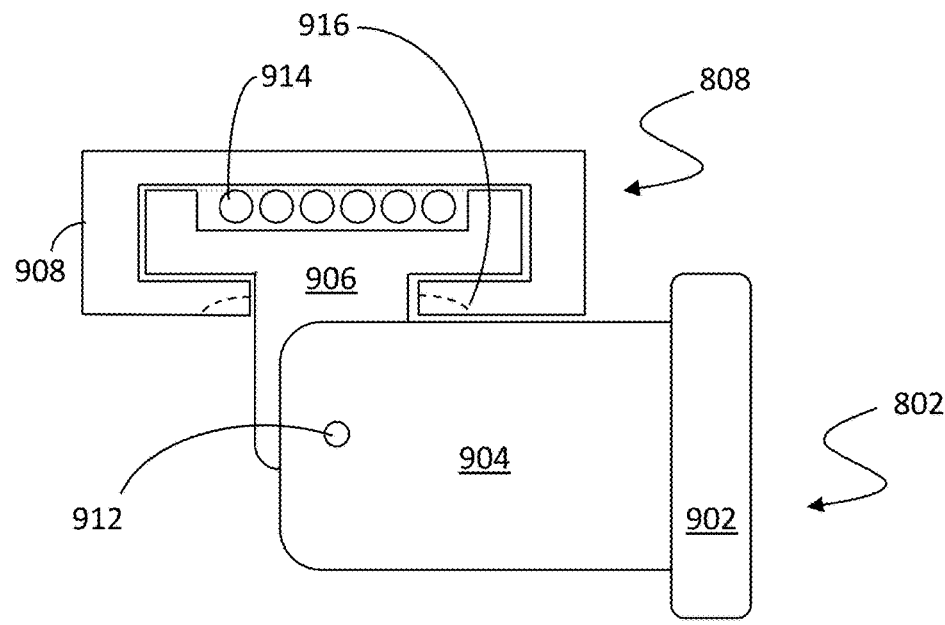
FIGS. 9A, 9B are schematic illustrations showing a handle system in different states of actuation according to an embodiment of the system described herein.
Figure 9B:
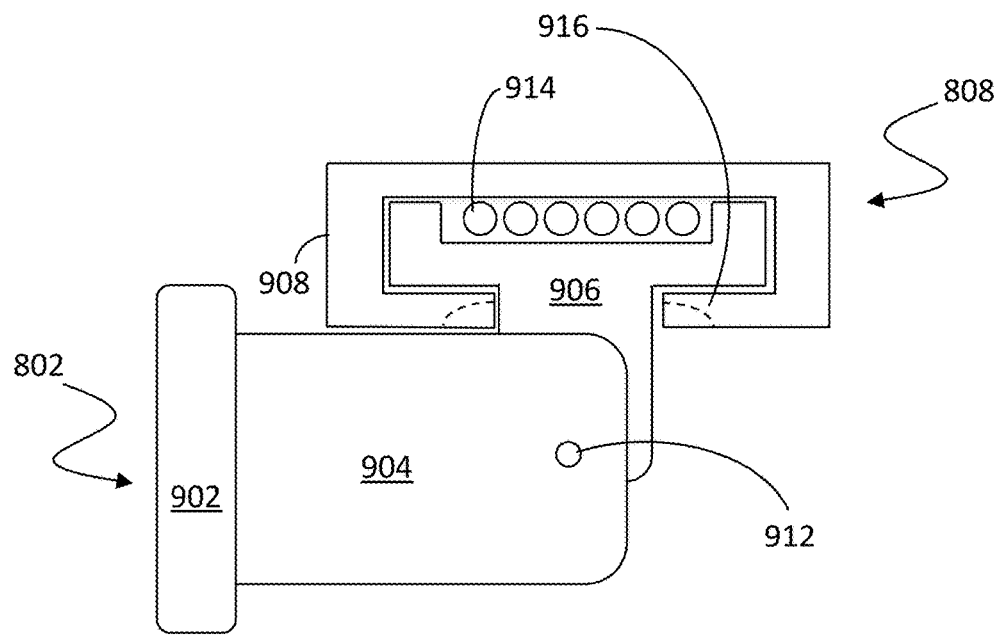

Referring to FIG. 9A, the crank arm 904 and handle 902 are shown having been rotated about the pin 912 to one side to a different position than that shown in FIG. 8. The position shown in FIG. 9A allows movement of the drive mechanism 906 within the control assembly housing 908 because the crank arm 904 is not engaged with a slot 916 in the housing. The handle 902 is rotatably attached to the crank arm 904. A user holds the handle 902 and moves the crank assemble 802 circularly about the inside of the control assembly 808 to wind or unwind the cable 914 about the control assembly housing 908. Moving the crank assembly 802 in one direction causes the source (not shown in FIG. 9A) to move toward the control assembly 808 while moving the crank assembly 802 in an other direction causes the source to move away from the control assembly 808. FIG. 9B illustrates that the crank arm 904 can be placed on an other side of the control assembly 808. Thus an operator can operate the crank assembly 802 with a left hand or a right hand without changing an orientation of the control assembly 808. In some embodiments, the crank arm 904 is urged by a spring (not shown) or similar to a position that inhibits movement of the cable 914 so that the cable 914 is locked (prevented from winding or unwinding) unless a user moves the crank arm 904 to one of the positions illustrated in FIG. 9A or 9B. Note that a relatively small distance between the control assembly housing 908, the cable 914 and the drive mechanism 906 allows the cable 914 to be pushed out of the control assembly 808 in a way that causes the source (not shown) to move away from the control assembly 808.

Figure 10:
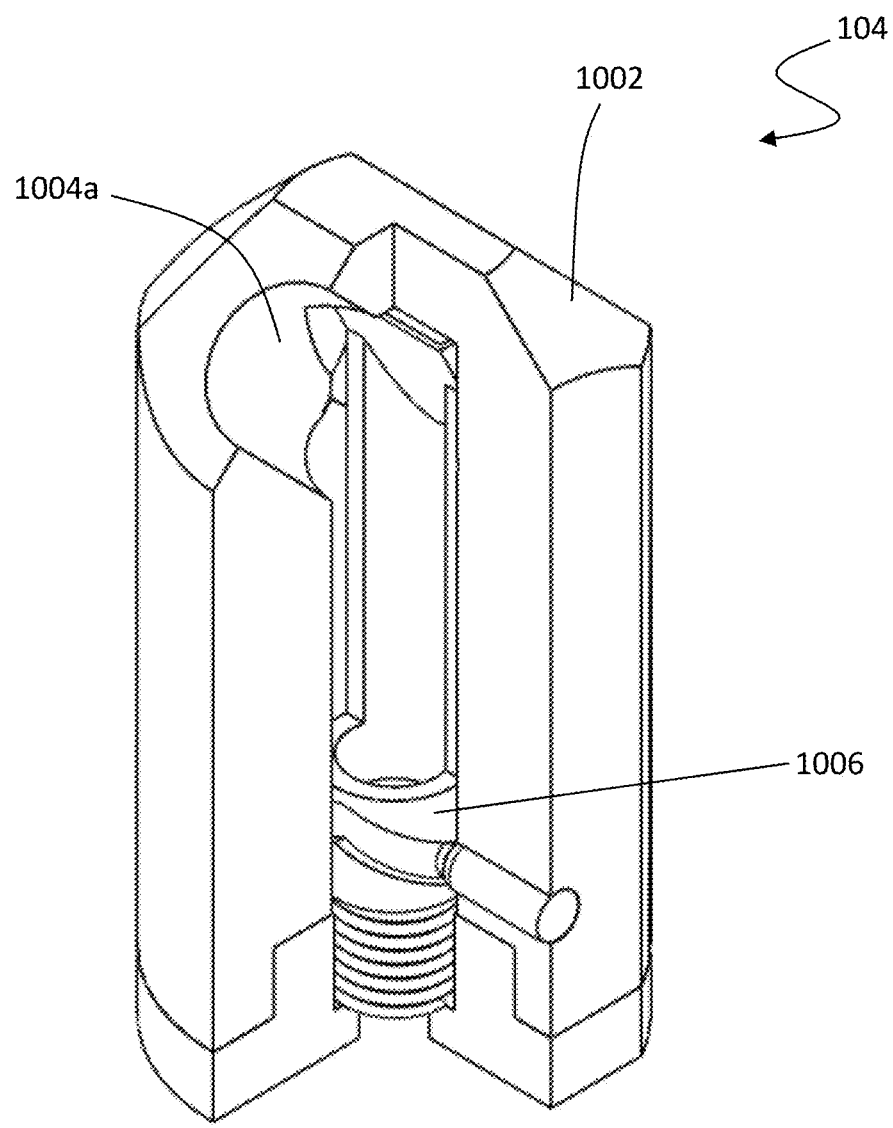
FIG. 10 is a schematic illustration of a switch for switching a cable used in a radiation delivery system according to an embodiment of the system described herein.

Referring to FIG. 10, the switch 104 of FIG. 1 is shown in more detail as a cutaway that includes a body 1002, a hole 1002a, and a switch sled 1006. A second hole is not shown in FIG. 10 because of portions removed by the cutaway. The hole 1002a is one of two holes in the switch 104. As explained in more detail elsewhere herein, a cable (not shown in FIG. 10) is provided through the switch sled 1006 and is caused to emerge through one of the holes in the switch 104 by operation thereof. The switch 104 may be used in connection with an exposure device having a single entrance, rather than a pass through design.

Figures 11A, 11B:
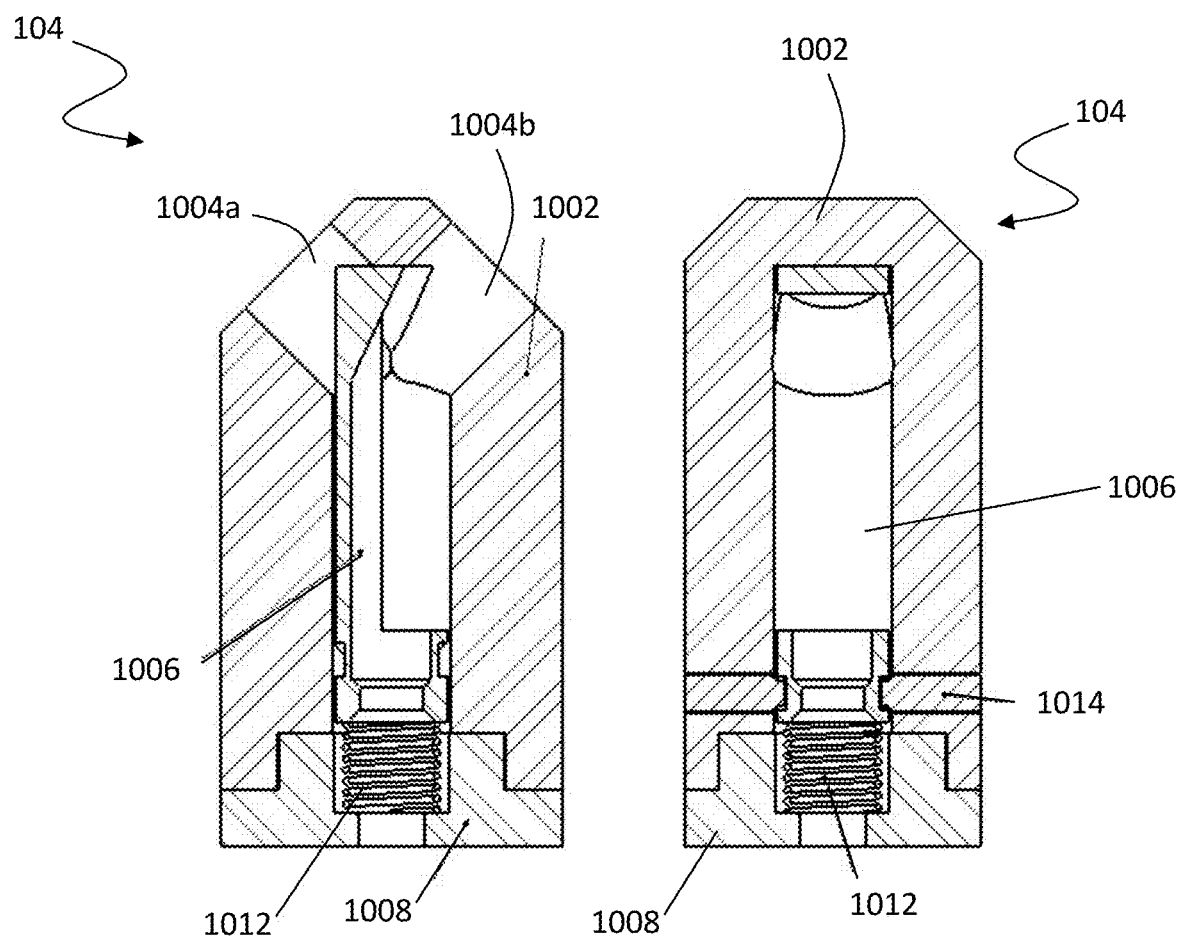
FIGS. 11A and 11B are schematic illustrations showing different views of a switch for switching a cable used in a radiation delivery system according to an embodiment of the system described herein.

Referring to FIG. 11A, the switch 104 is shown in more detail with the hole 1004a and an other hole 1004b, discussed above in connection with FIG. 10 but not shown therein. A retaining block 1008 is used to retain the switch sled 1006 in the body 1002. A cable (not shown) entering the switch 104 through a hole in the retaining block 1008 is guided to one of the two holes 1004a, 1004b by the switch sled 1006. A switch spring 1012 biases the switch sled 1006 toward the holes 1004a, 1004b.

Referring to FIG. 11B, the switch 104 is shown at a ninety degree angle from the view of FIG. 11A. A retaining pin 1014, which is described in more detail elsewhere herein, may allow the switch sled 1006 to rotate within the switch body 1002 in one direction, but not another and may be used to facilitate switching between the holes 1004a, 1004b. Rotation of the switch sled 1006 in the switch body 1002 is described in more detail elsewhere herein.

Figure 12A:
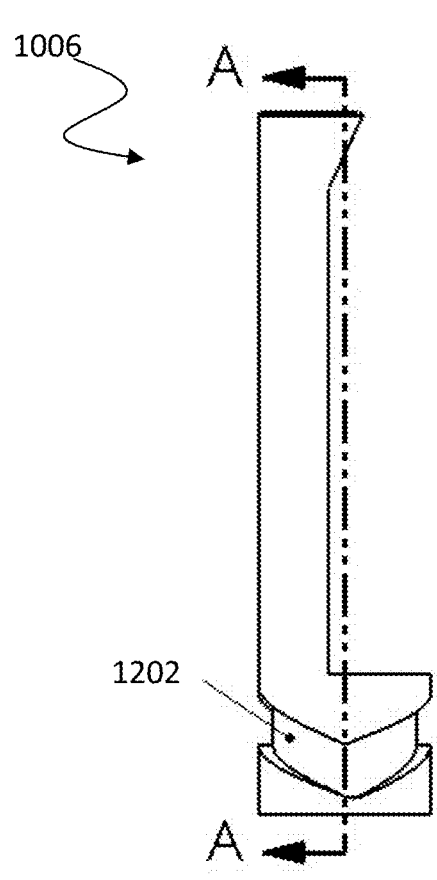
FIGS. 12A and 12B are schematic illustrations showing different views of a switch sled used with a switch for switching a cable used in a radiation delivery system according to an embodiment of the system described herein.
Figure 12B:
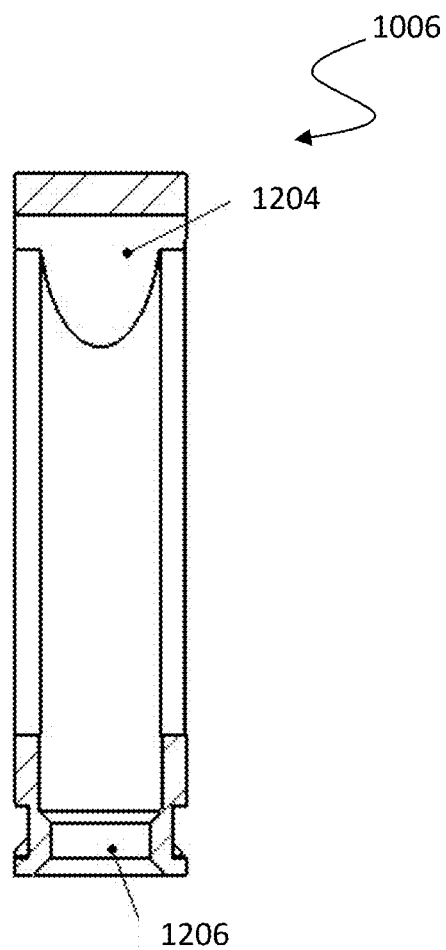

Referring to FIGS. 12A and 12B, the switch sled 1006 is shown in more detail as including a clicker cam 1202, a guide ramp 1204, and a source assembly catch 1206. The clicker cam 1202 rests against the retaining pin 1014 (shown in FIG. 11B) and is used to actuate the switch 104, as described in more detail elsewhere herein. The guide ramp 1204 guides a cable (not shown) through one of the two holes 1004a, 1004b (shown in FIGS. 11A, 11B), depending upon which of the two holes 1004a, 1004b is facing the guide ramp 1204.

The hole in the retaining block 1008 may be coupled to the conduit 106 of FIG. 1. One of the holes 1004a, 1004b may be coupled to the guide tube 112 of FIG. 1 which the other one of the holes 1004a, 1004b may be coupled to the conduit that leads to the exposure chamber 102 of FIG. 1. One or both ends of the holes 1004a, 1004b may be threaded to provide a secure, but removable, connection. Any other appropriate connection mechanism may be used.

In operation, an operator may wind a cable having a source assembly through the switch 104. The source assembly engages with the source assembly catch 1206 to urge the switch sled 1006 away from the holes 1004a, 1004b. Note that any appropriate component may be used to engage the source assembly catch 1206, such as a connector on the end of the cable or a component of the source assembly. As the switch sled 1006 moves away from the holes 1004a, 1004b, the clicker cam 1202 and the retaining pin 1014 cause the switch sled 1006 to rotate within the body 1002 in a manner similar to operation of a conventional ball point pen. Rotation of the switch sled 1006 causes the guide ramp 1204 to face a different one of the holes 1004a, 1004b. Thus, retracting the source assembly into the switch 104 and against the source assembly catch 1206 actuates the switch 104. Note that the switch spring 1012 causes the switch sled 1006 to move toward the holes 1004a, 1004b when the source assembly is no longer urged against the source assembly catch 1206. The switch sled 1006 may rotate further in connection with moving toward the holes 1004a, 1004b. In an embodiment herein, the clicker cam 1202 and the retaining pin 1014 may cause the switch sled 1006 to rotate ninety degrees when the switch sled 1006 moves away from the holes 1004a, 1004b and to rotate another ninety degrees in a same direction when the switch sled 1006 moves back toward the holes 1004a, 1004b. After actuation, the source assembly may leave the switch 104 by whichever one of the holes 1004a, 1004b is faced by the guide ramp 1204.

The switch 104 and components may be constructed with many appropriate materials, including most metals, plastics, and other sturdy materials. In an embodiment, the switch may be constructed using a combination of titanium and stainless steels because the physical properties of weight, strength, and resistance to degradation thereof. The body 1002 and the retaining block 1008 may be made of titanium, the switch sled 1006 and the retaining pins 1014 may be made of 316 stainless steel, and the switch spring 1012 may be made of stainless steel. Note also that the body 1002 and the retaining block 1008 may be made of tungsten to provide radiation shielding.

Figure 13A:
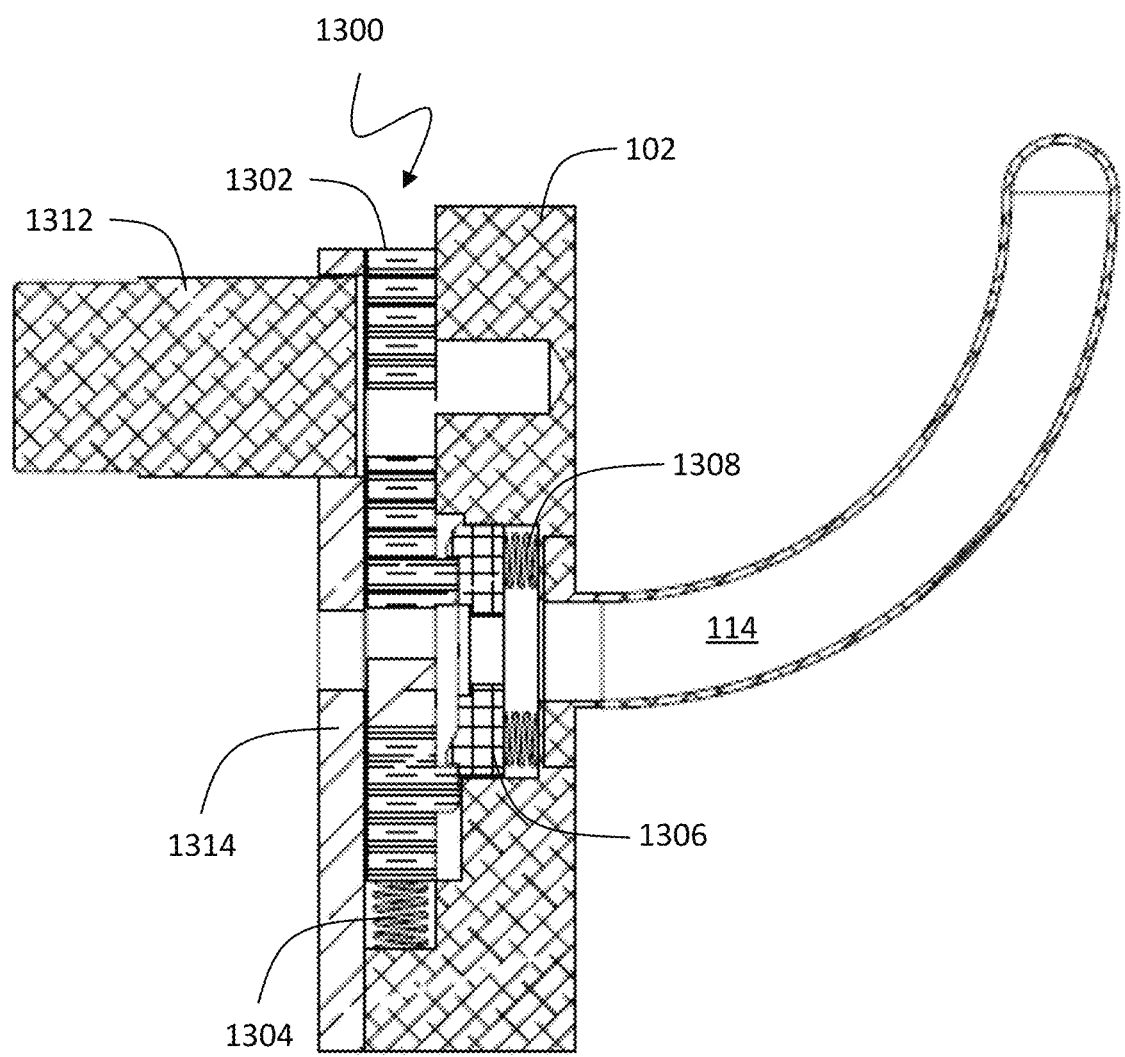
FIGS. 13A and 13B are schematic illustrations of an automatic securing mechanism in an unlocked position according to embodiments of the system described herein.

Referring to FIG. 13A, an automatic securing mechanism (ASM) 1300 includes a locking bar 1302, a locking bar spring 1304, a securing block 1306, a securing block spring 1308, a mechanical lock 1312, and a faceplate 1314, all of which are coupled to a portion of the exposure container 102 that includes an opening for the J-channel 114. The ASM 1300 automatically secures the source assembly in a fully shielded position. The ASM 1300 is an alternative to the embodiment illustrated in connection with FIGS. 5A-5C and 6A-6C and described above. The ASM 1300 may be locked or unlocked, as described in more detail elsewhere herein.

Figure 13B:
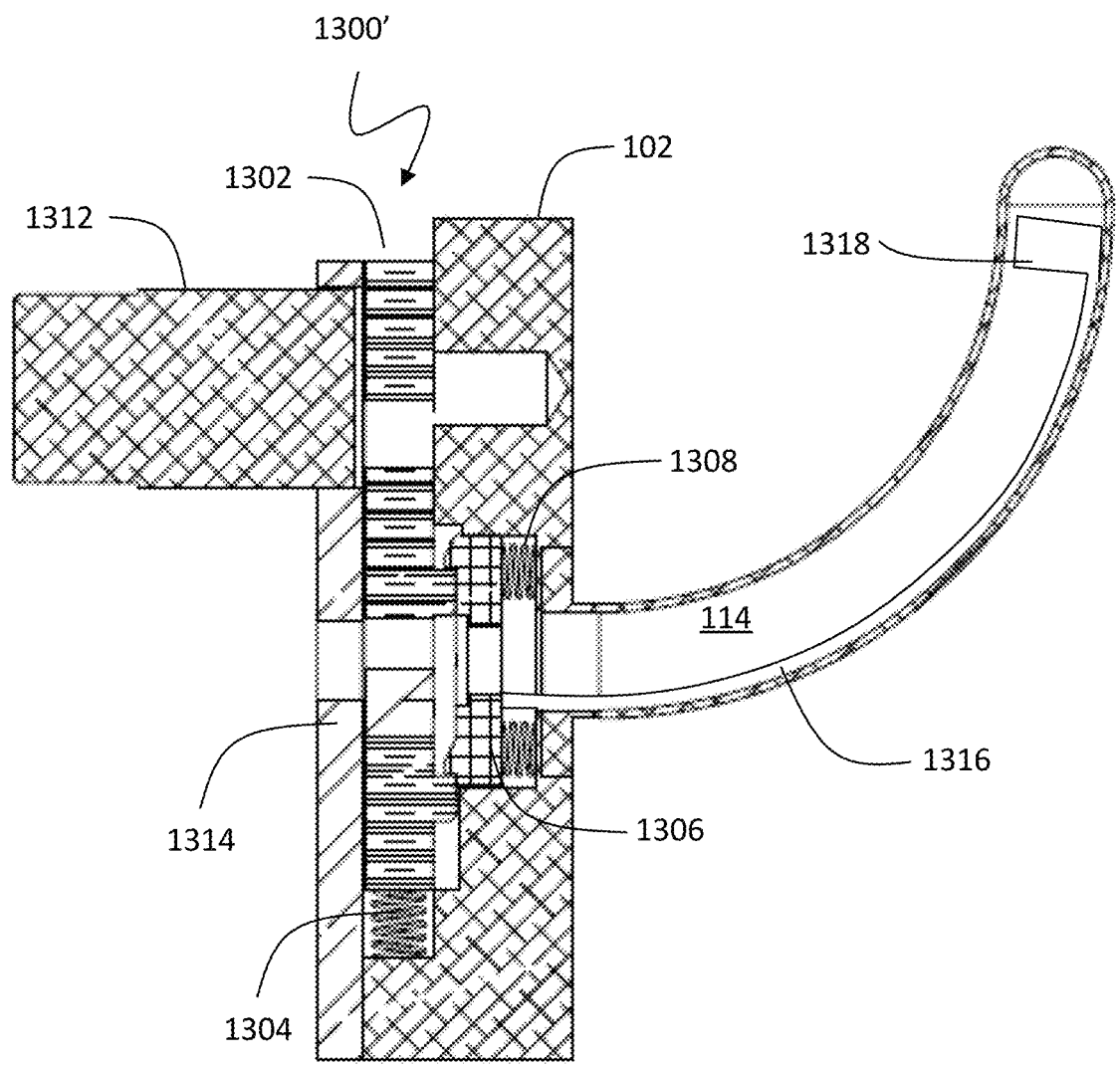

Referring to FIG. 13B, an alternative embodiment includes an ASM 1300', which is like the ASM 1300 of FIG. 13A. The ASM 1300' includes a sled 1316 that is disposed in a bottom portion of the J-channel 114 and is attached to the securing block 1306. The sled 1316 includes an end portion 1318 that interacts with the source assembly (not shown) to facilitate automatic locking of the ASM 1300'. Operation of the alternative embodiment is described in more detail elsewhere herein.

Figure 14A:
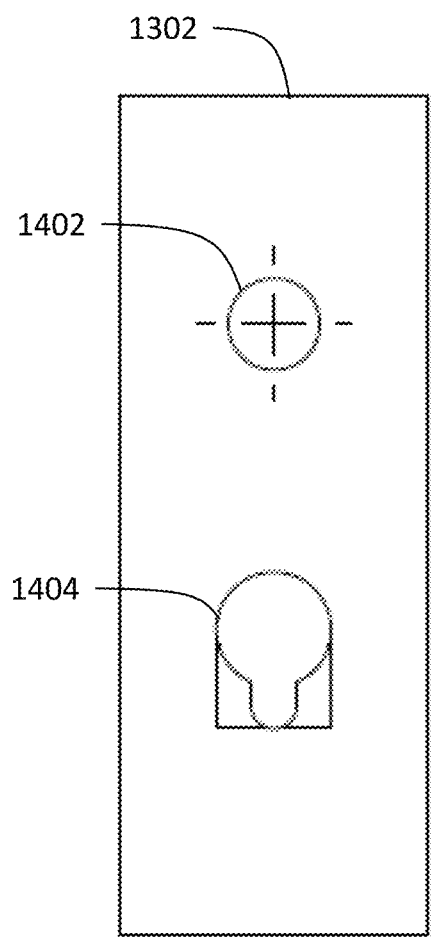
FIGS. 14A and 14B are schematic illustrations of a locking bar used with an automatic securing mechanism according to an embodiment of the system described herein.
Figure 14B:
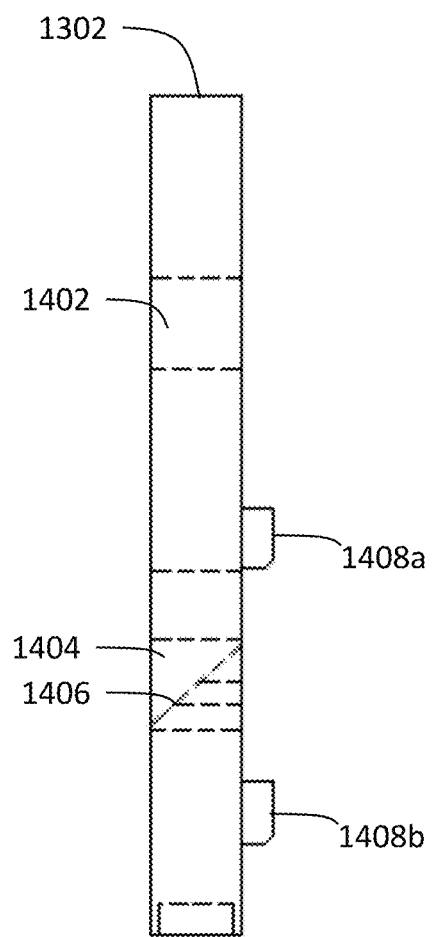

Referring to FIGS. 14A and 14B, the locking bar 1302 is shown in more detail as including a first hole 1402 that accommodates a plunger for the mechanical lock 1312 and a second hole 1404 that accommodates a source assembly (not shown). The second hole 1404 is shaped so that, when an upper portion of the hole 1404 having a relatively large opening is aligned with the J-channel 114, the source assembly can pass in and out of the J-channel 114, but when a lower portion of the hole 1404 having a relatively small opening is aligned with the J-channel 114, the source assembly can not pass in and out of the J-channel 114. As discussed elsewhere herein, the source assembly may include beads or similar components. The lower portion of the hole 1404 may be large enough to accommodate a cable (not shown) coupled to the source assembly, but not large enough to allow passage of a bead (or similar). FIG. 14B shows a side view of the locking bar 1302 and includes the holes 1402, 1404 as well as a chamfered surface 1406 of the hole 1404. The locking bar 1302 also includes two protrusions 1408a, 1408b. The purpose of the chamfered surface 1406 and the protrusions 1408a, 1408b is discussed in more detail elsewhere herein.

Figures 15A, 15B:
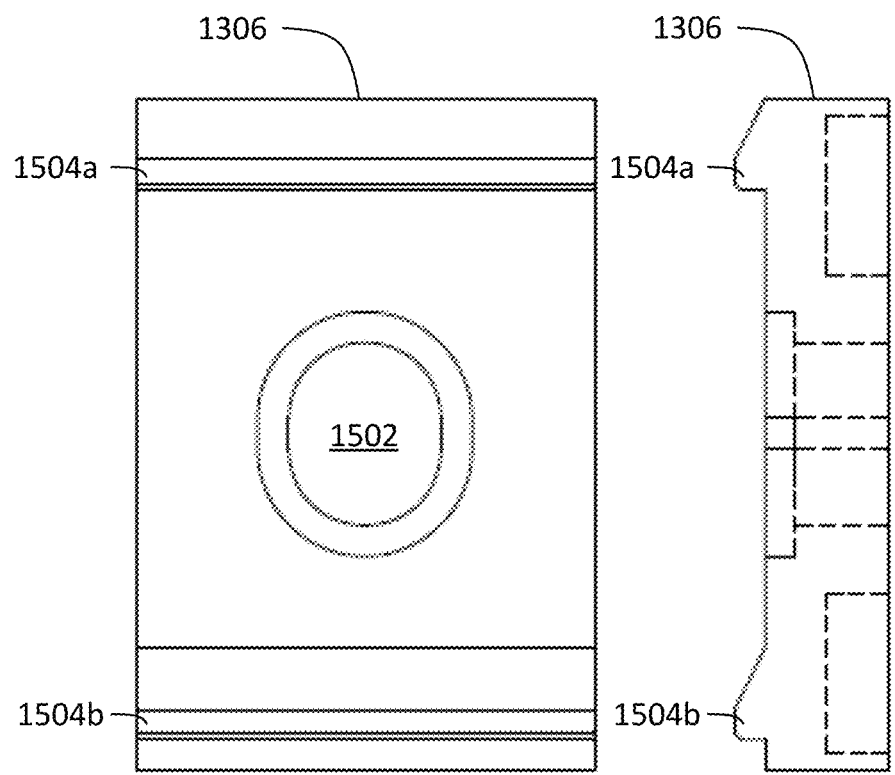
FIGS. 15A and 15B are schematic illustrations of a securing block used with an automatic securing mechanism according to an embodiment of the system described herein.

Referring to FIGS. 15A and 15B, the securing block 1306 is shown in more detail as including an opening 1502 that accommodates a source assembly (not shown). The securing block 1306 also includes two notches 1504a, 1504b. The notches 1504a, 1504b of the securing block 1306 engage with the protrusions 1408a, 1408b of the locking bar 1302, as described in more detail elsewhere herein.

Figure 16A:
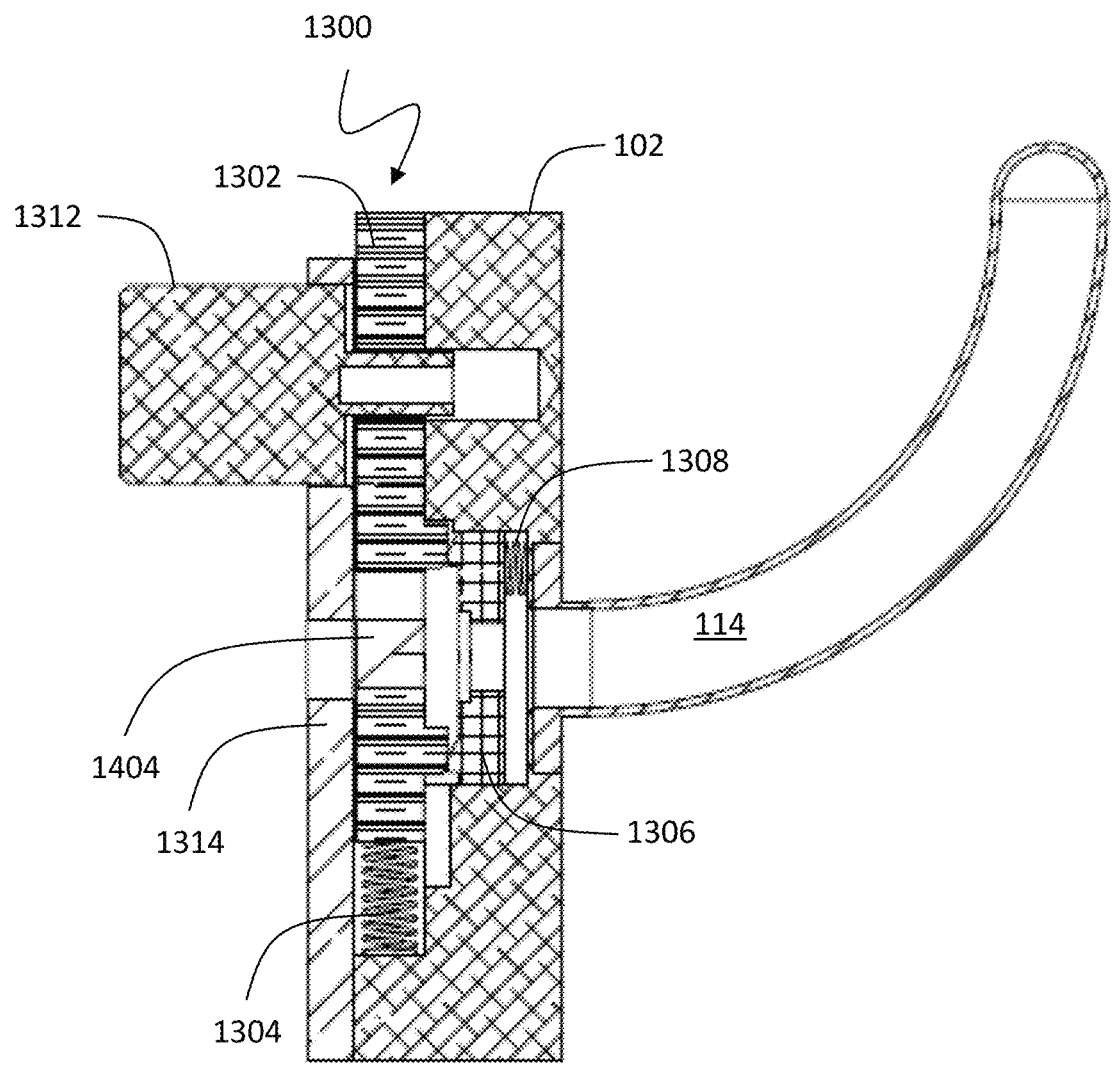
FIGS. 16A and 16B are schematic illustrations of an automatic securing mechanism in a locked position according to embodiments of the system described herein.

Referring to FIG. 16A, the ASM 1300 is illustrated in a locked position that prevents a source assembly (not shown) from being removed from the J-channel 114. Note that alignment of the locking bar 1302 causes the small portion of the hole 1404 to align with the open end of the J-channel 114. As discussed elsewhere herein, the small portion of the hole 1404 inhibits passage of the source assembly. Note that FIG. 14 shows the ASM 1300 in an unlocked state.

In operation, the ASM 1300 may begin in a locked or unlocked state prior to inserting the source assembly into the J-channel 114. If the ASM 1300 begins in a locked state (such as the state shown in FIG. 16A), the ASM 1300 may be transitioned to an unlocked state by urging the locking bar 1302 toward the locking bar spring 1304. The protrusions 1408a, 1408b of the locking bar 1302 engage with chamfered edges of the notches 1504a, 1504b of the securing block 1306 to cause the securing block 1306 to move towards the J-channel 114. Note that, while the locking bar 1302 is urged toward the locking bar spring 1304, the locking bar spring 1304 provides a counter-force for the movement of the locking bar 1302 and the securing block spring 1308 provides a counter-force for a movement of the securing block 1306. Eventually the protrusions 1408a, 1408b of the locking bar 1302 will move past the notches 1504a, 1504b of the securing block 1306 so that the securing block spring 1308 causes the securing block 1306 to move towards the locking bar 1302. The protrusions 1408a, 1408b of the locking bar 1302 engage with flat edges of the notches 1504a, 1504b of the securing block 1306 to maintain the locking bar in an unlocked position, as illustrated in FIG. 13A. An alternative mechanism for unlocking the ASM 1300 uses the chamfered surface 1406 of the hole 1404. The source assembly may push against the chamfered surface 1406 to cause the locking bar 1302 to move downward without a need to apply any other force to the locking bar 1302.

Once the source of the source assembly is moved into the J-channel 114, the ASM 1300 may be locked by having a larger portion of the source assembly (e.g., a bead or similar) be larger than the hole 1502 in the securing block 1306. The larger portion of the source assembly is urged against the securing block 1306 to move the securing block toward the J-channel 114. Once the amount of movement of the securing block 1306 exceeds a height of the notches 1504a, 1504b of the securing block 1306, the locking bar spring 1304 causes the locking bar 1302 to move so that the ASM 1300 is in a locked position, such that illustrated in FIG. 16A.

Figure 16B:
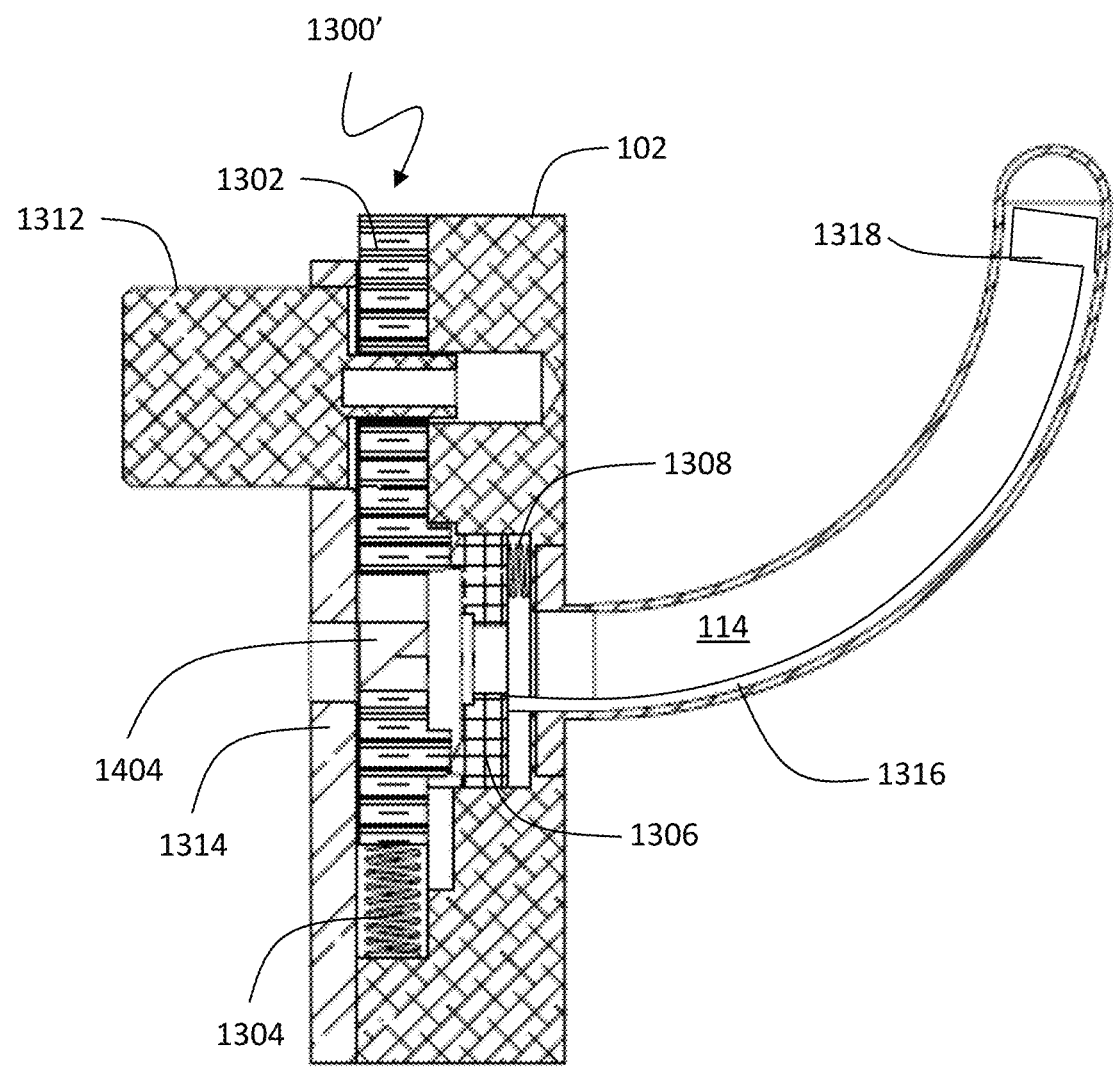

FIG. 13B illustrates the alternative embodiment of the ASM 1300', described above. The ASM 1300' uses the sled 1316 to facilitate automatic locking thereof. The source assembly (not shown) is inserted into the J-channel 114 and passes over the sled 1316 and eventually engages the end 1318 of the sled 1316 to urge the securing block 1306 away from the locking bar. Once the amount of movement of the securing block 1306 exceeds a height of the notches 1504a, 1504b of the securing block 1306, the locking bar spring 1304 causes the locking bar 1302 to move so that the ASM 1300' is in a locked position, such that illustrated in FIG. 16B. The ASM 1300' may be unlocked in a manner similar to unlocking the ASM 1300', discussed elsewhere herein.

Once the ASM 1300 (or the ASM 1300') is in a locked position, the mechanical lock 1312 may be engaged to provide a plunger through the hole 1402 in the locking bar 1302 and a corresponding cavity in the exposure container 102 to prevent movement of the locking bar 1302 and thus prevent unlocking of the ASM 1300 (or the ASM 1300'). The ASM 1300 (or the ASM 1300') may be subsequently unlocked as described herein following unlocking (disengaging) the mechanical lock 1312.

In some embodiments, the mechanical lock 1312 may be a barrel plunger lock. When the mechanical lock 1312 is locked, a face of the mechanical lock 1312 may be depressed and a plunger may protrude from a back of the mechanical lock 1312. In some embodiments, turning a key inside the mechanical lock 1312 springs the faceplate 1314 outward and retracts the plunger, allowing the locking bar 1302 to be depressed. In some cases, when the ASM 1300 is in a locked configuration, the mechanical lock 1312 may be locked by depressing the faceplate 1314, causing the lock plunger to protrude and pierce the locking bar 1302, thus preventing the locking bar 1302 from being moved. Note that the mechanical lock 1312 may not be locked while the ASM 1300 is in an unlocked configuration because the plunger of the mechanical lock 1312 does not aligned with the hole 1402 in the locking bar 1302.

In an embodiment herein, a top portion of the locking bar 1302 may be colored green and imprinted with "Closed" (or similar). The portion of the exposure container 102 directly behind the top portion of the locking bar 1302 may be colored red and imprinted with "Open" (or similar). Such a mechanism may establish a visual indication of a current configuration (locked or unlocked) of the ASM 1300 or the ASM 1300'.

The ASM 1300 (or the ASM 1300') could be constructed with many materials, including most metals, plastics, and other study materials. An embodiment herein uses a combination of titanium and stainless steels because of the physical properties of weight, strength, and resistance to degradation thereof. In an embodiment, the locking bar 1302, the securing block 1306, the locking bar spring 1304, and the securing block spring 1308 are made of 316 stainless steel, the portion of the exposure container 102 corresponding to the ASM 1300 (or the ASM 1300') and the faceplate 1314 are made out of titanium, and the mechanical lock 1312 may be stainless steel. The securing block 1306 may also be made from tungsten to provide additional radiation shielding. The sled 1316 for the ASM 1300' may be manufactured using similar materials.

Figure 17:
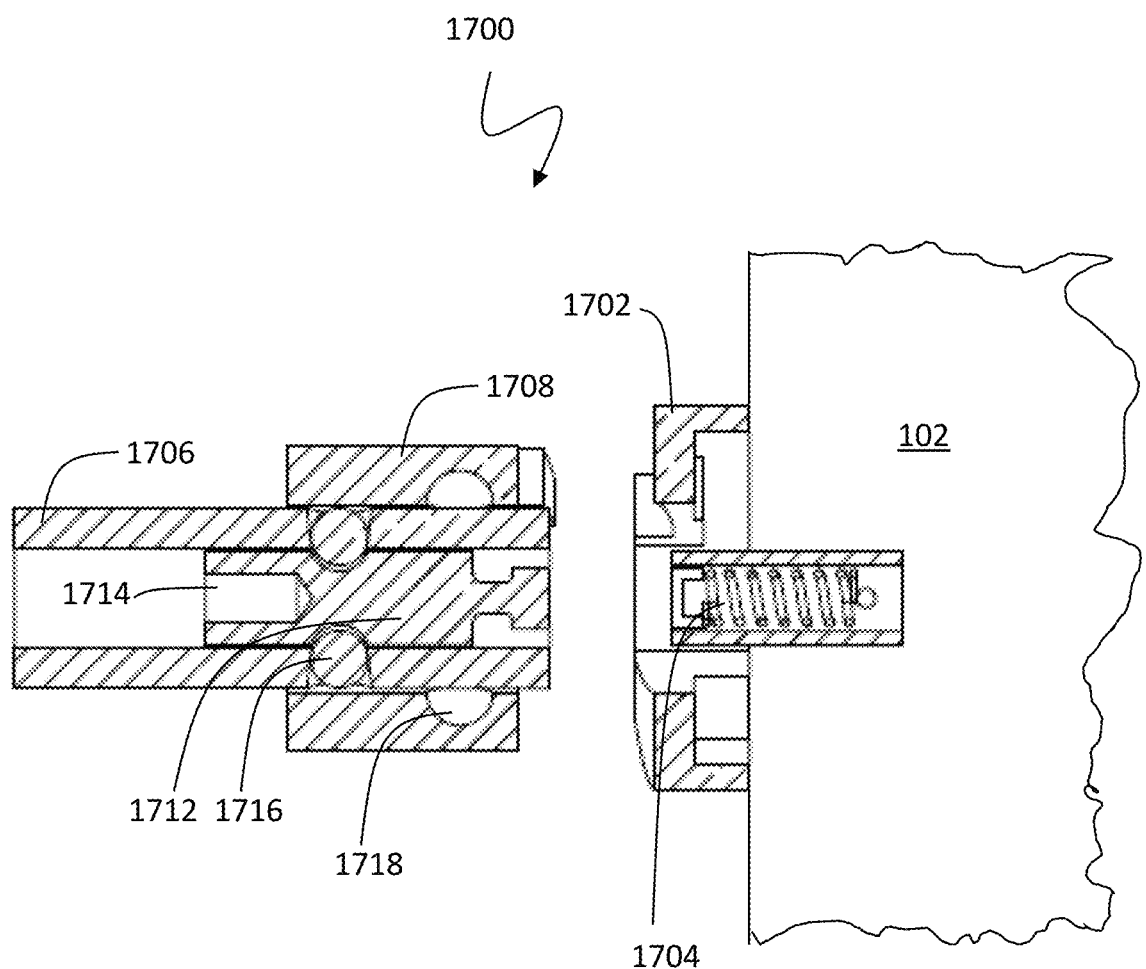
FIG. 17 is a schematic illustration of a control adaptor assembly in an uncoupled state according to an embodiment of the system described herein.

Referring to FIG. 17, a control adaptor assembly 1700 in an uncoupled state may be used to connect a control conduit (such as the conduit between the switch 104 and the exposure container 102, described above) to the exposure container 102 while simultaneously connecting a drive cable connector to a source assembly connector. As discussed elsewhere herein, in some instances, the switch 104 is connected directly to the exposure container 102 and there is no conduit therebetween. The connections may be made by pressing two sections of the control adaptor assembly 1700 together and rotating 90°. Having the connections secure simultaneous is advantageous. The control adaptor assembly 1700 is like the connectors 302, 304 described above in connection with FIG. 3 and FIG. 4.

A device boss 1702 is fixedly attached (e.g., welded) to the exposure container 102. A source assembly connector 1704 is provided in the device boss 1702 and provides an attachment point for a source assembly (not shown) within the exposure container 102. Conduit lugs 1706 are attached to a control conduit (not shown) by, for example, a threaded connection, crimping, etc. A control adaptor collar 1708 is slidably coupled to the conduit lugs 1706. The device boss 1702 provides an attachment point for the control color adaptor 1708 and the conduit lugs 1706.

A drive cable connector 1712 is disposed in the conduit lugs 1706 and provides a mechanism for connecting the drive cable (not shown) to the source assembly (not shown). A drive cable crimp area 1714 is a cavity at an end of the drive cable connector 1712 into which the drive cable is inserted and then crimped for attachment. Of course, any other mechanism for attachment may be used. The conduit lugs 1706 also include locking balls 1716, which prevent movement of the drive cable connector 1712. The control adaptor collar 1708 includes recesses 1718 that accept the locking balls 1716 to allow movement of the drive cable connector 1712 after a proper connection is made, as explained in more detail elsewhere herein.

Figure 18:
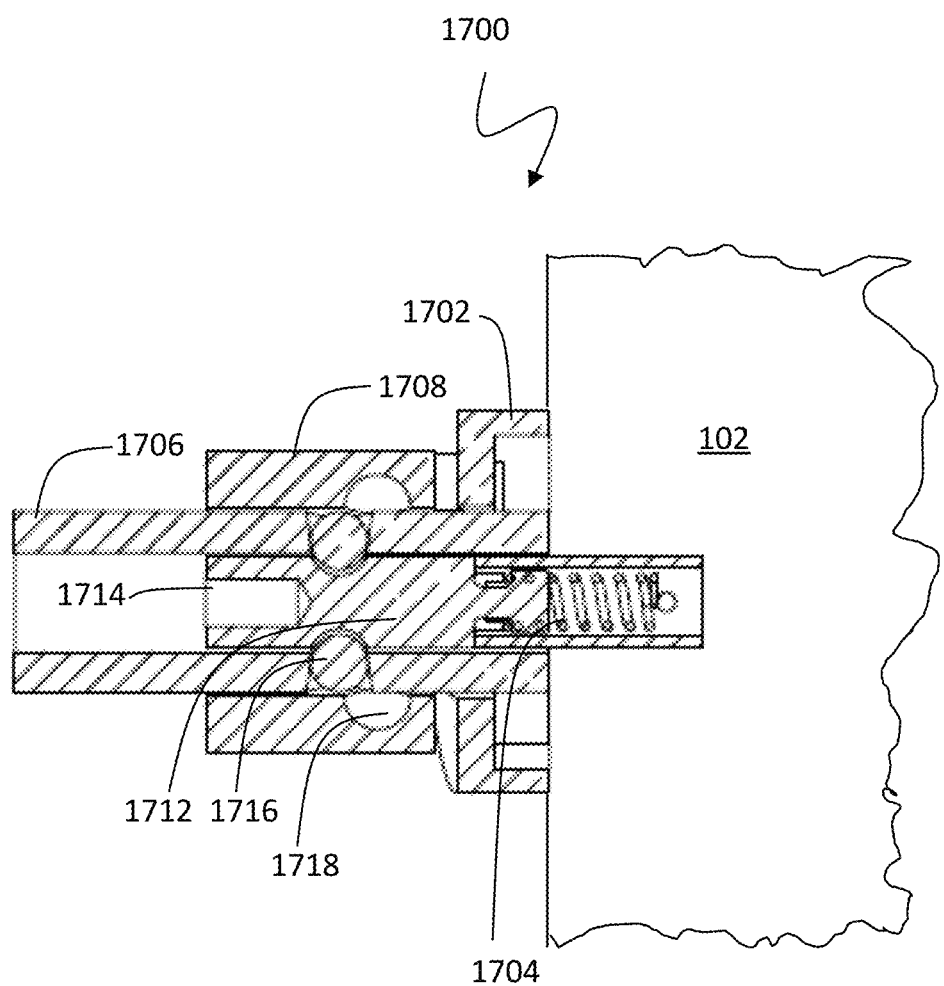
FIG. 18 is a schematic illustration of a control adaptor assembly in an unrotated state according to an embodiment of the system described herein.

Referring to FIG. 18, the control adaptor assembly 1700 in an unrotated state is shown with the device boss 1702 in contact with the conduit lugs 1706. When the conduit lugs 1706 and the device boss 1702 are properly aligned, an operator can push the conduit lugs 1706 into the device boss 1702 to cause the control adaptor collar 1708 to move laterally along the conduit lugs 1706. In an embodiment herein, the conduit lugs 1706 may be biased with a spring (not shown) that urges the control adaptor collar 1708 to move in a direction toward the device boss 1702. Note that, the position shown in FIG. 18, the drive cable connector 1712 has connected with the source assembly connector 1704. However, the locking balls 1716 still inhibit movement of the drive cable connector 1712.

Figure 19:
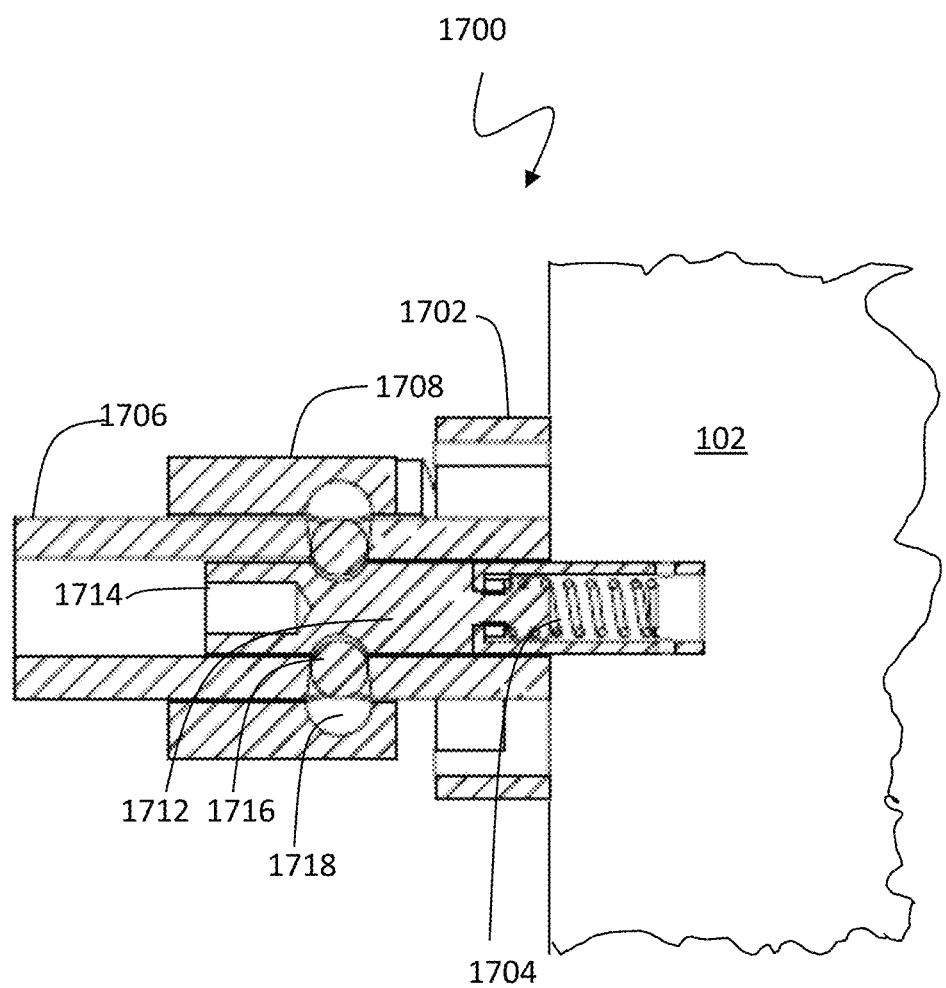
FIG. 19 is a schematic illustration of a control adaptor assembly in a connected state according to an embodiment of the system described herein.

Referring to FIG. 19, the control adaptor assembly 1700 in a connected state is shown fully connected after the operator has rotated the conduit lugs 1706 to make a firm attachment between the conduit lugs 1706 and the device boss 1702. In an embodiment herein, providing secure attachment by rotating the conduit lugs 1706 after making contact with the device boss 1702 causes the conduit lugs 1706 to move laterally. Further lateral movement of the conduit lugs causes the recesses 1718 to align with the locking balls 1716. The locking balls are biased (e.g., by a spring) to cause the locking balls to move into the recesses 1718 (not shown in FIG. 19). Once the locking balls 1716 are in the recesses 1718, the drive cable connector 1712 may be moved laterally to allow operating of the device.

The control adaptor assembly 1700 could be constructed with many materials, including most metals, plastics, and other sturdy materials. An embodiment herein uses a combination of titanium and stainless steels because of the physical properties of weight, strength, wear resistance and resistance to degradation thereof. In an embodiment herein, the control adaptor collar 1708, the conduit lugs 1706, and the device boss 1702 may be made from 316 stainless steel, possibly coated while the drive cable connector 1712 and the source assembly connector 1704 may be made from 420 stainless steel, that also may be possibly coated.

Figure 20A:
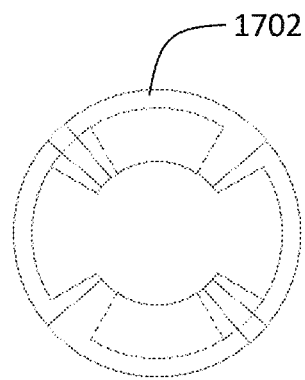
FIGS. 20A-20C are end views of components of a control adaptor assembly according to an embodiment of the system described herein.
Figure 20B:
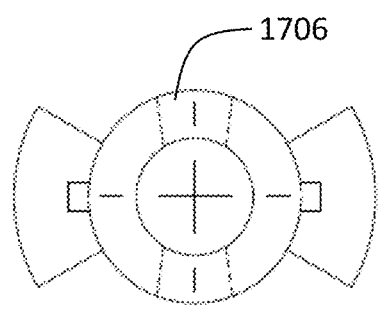
Figure 20C:
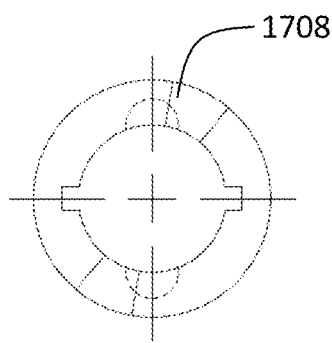

Referring to FIGS. 20A-20C, an end view of each of the device boss 1702, the conduit lugs 1706, and the control adaptor collar 1708 is shown. Of course, it is possible to use any alternative component having an appropriate shape, etc. to provide the functionality described herein.

Referring to FIGS. 21A-21E, an alternative embodiment of a control adaptor assembly 2100 may be used to connect a control conduit (such as the conduit between the switch 104 and the exposure container 102, described above, not shown in FIGS. 21A-21E) to the exposure container 102 (not shown in FIGS. 21A-21E) while simultaneously connecting a drive cable connector to a source assembly connector. The control adaptor assembly 2100 includes a control adaptor 2102, which is provided at an end of the control conduit and a boss 2104 that mates with the control adaptor 2102. The boss 2104 may be attached to the exposure container 102.

The control adaptor 2102 includes an inner portion 2106 that moves co-axially within the control adaptor 2102. The inner portion 2106 has a pair of tines 2108a, 2108b that mate with corresponding gaps 2112a, 2112b in the boss 2104. In an embodiment herein, a control adaptor spring (not shown) may urge the inner portion 2106 within the control adaptor 2102 in a coaxial direction toward the boss 2104 (i.e., to the right in FIGS. 21A-21D). The control adaptor 2102 mates with and attaches to the boss by aligning the tines 2108a, 2108b with the gaps 2112a, 2112b and rotating the control adaptor 2102. Ramps on mating surfaces of the control adaptor 2102 and the boss 2104 cause the control adaptor 2102 to press against the boss 2104 when rotated. A force of the control adaptor spring (not shown) causes the control adaptor 2102 and the boss 2104 to mate snugly.

A male source connector 2122 passes through the control adaptor 2102. The male source connector 2122 includes a knobby end portion and is fixedly coupled to the drive cable 218 (not shown in FIGS. 21A-21E). A female source connector 2124 passes through the boss 2104. The female source connector 2124 includes a spring (not shown) in an end thereof that accepts the knobby end portion of the male source connector 2122. The male source connector 2122 connects to the female source connector 2124 when the connectors 2122, 2124 are pressed together axially. The male source connector 2122 may be disconnected from the female source connector 2124 by applying axial force to separate the connectors 2122, 2124.

Figure 21A:
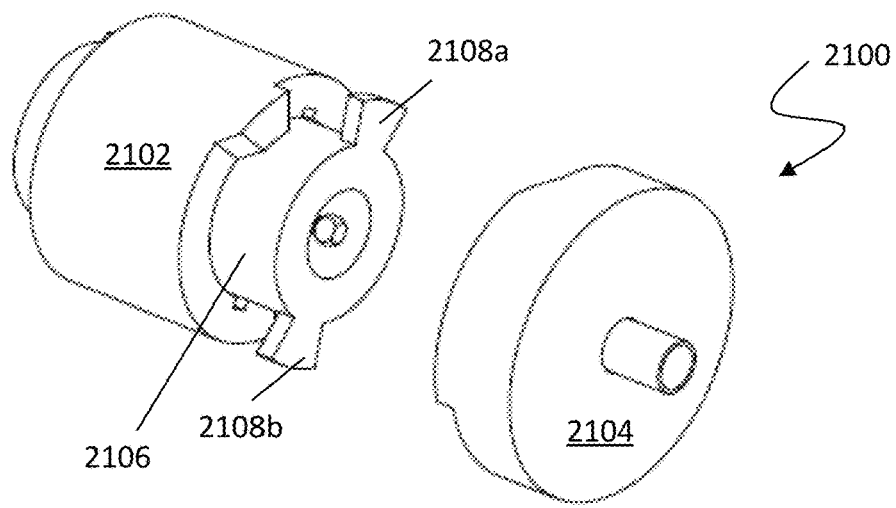
FIGS. 21A-21E are schematic illustrations of an alternative control adaptor according to an embodiment of the system described herein.
Figure 21B:
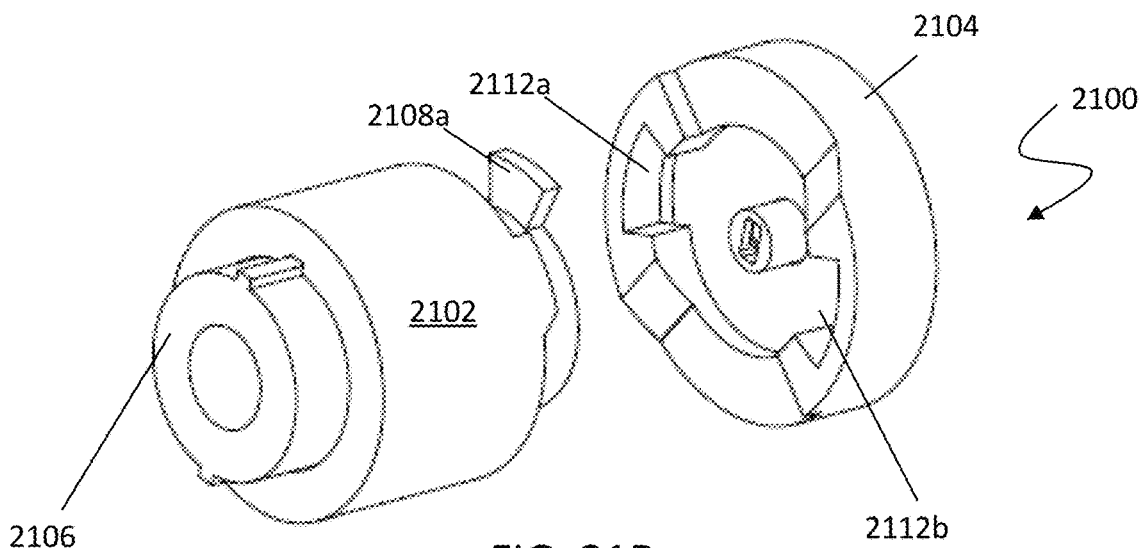
Figure 21E:
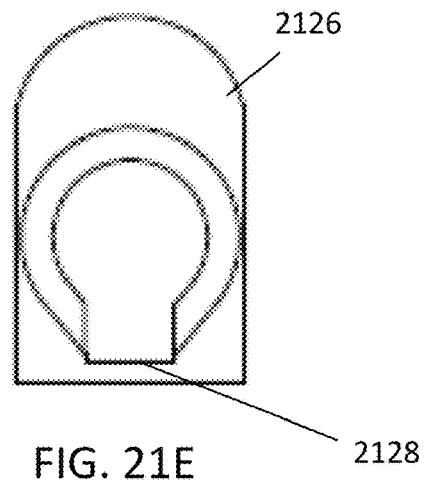
Figure 21C:
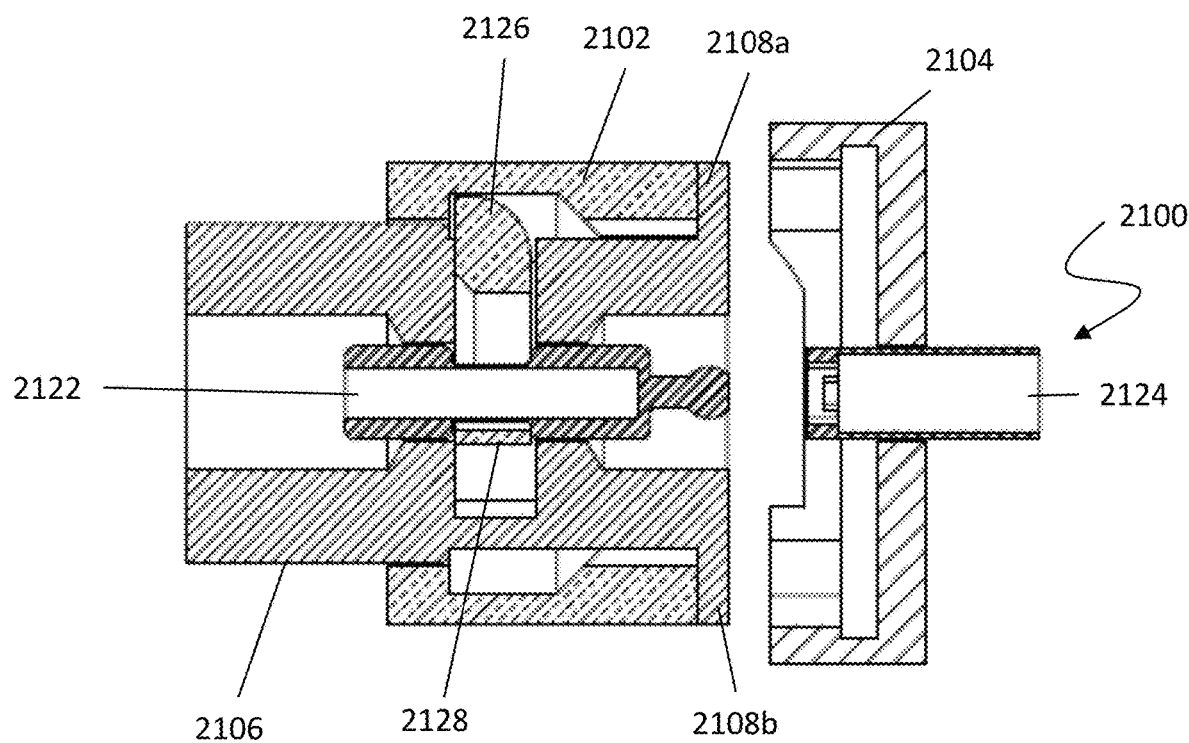
Figure 21D:
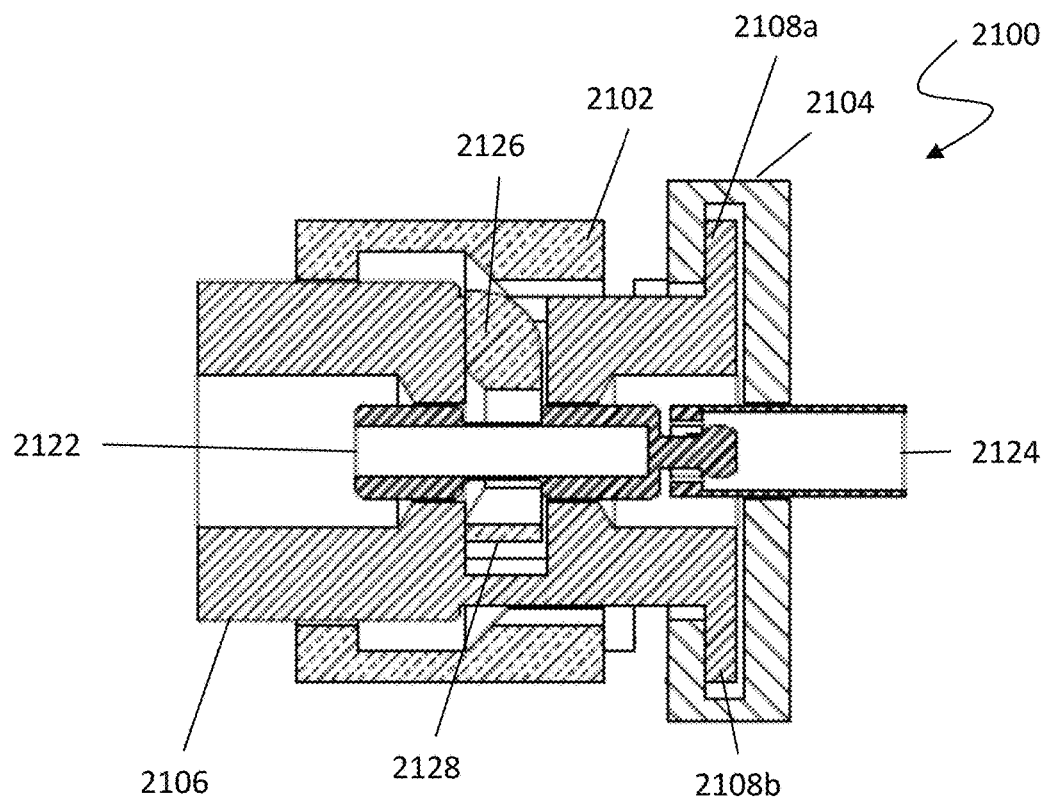

A locking bar 2126 prevents movement of the male source connector 2122 within the control adaptor 2102. The locking bar is shown in FIG. 21E as including a bottom portion 2128. In FIG. 2C, the locking bar 2126 is shown in a position (upwards in FIG. 21C) that prevents axial movement of the male source connector 2122. In an embodiment herein, the locking bar may be urged upwards by a spring (not shown). As the inner portion 2106 of the control adaptor moves towards the boss 2104 (in response to rotating the control adaptor 2102, described above), a ramp on an interior portion of the control adaptor 2102 causes the locking bar 2126 to move downward. Eventually, the locking bar 2126 is positioned so that the wider, circular portion thereof aligns with the male source connector 2122 so that the male source connector 2122 and the female source connector 2124, which is attached to the male source connector 2122, are free to move axially laterally within the control adaptor assembly 2100.

Figure 22A:
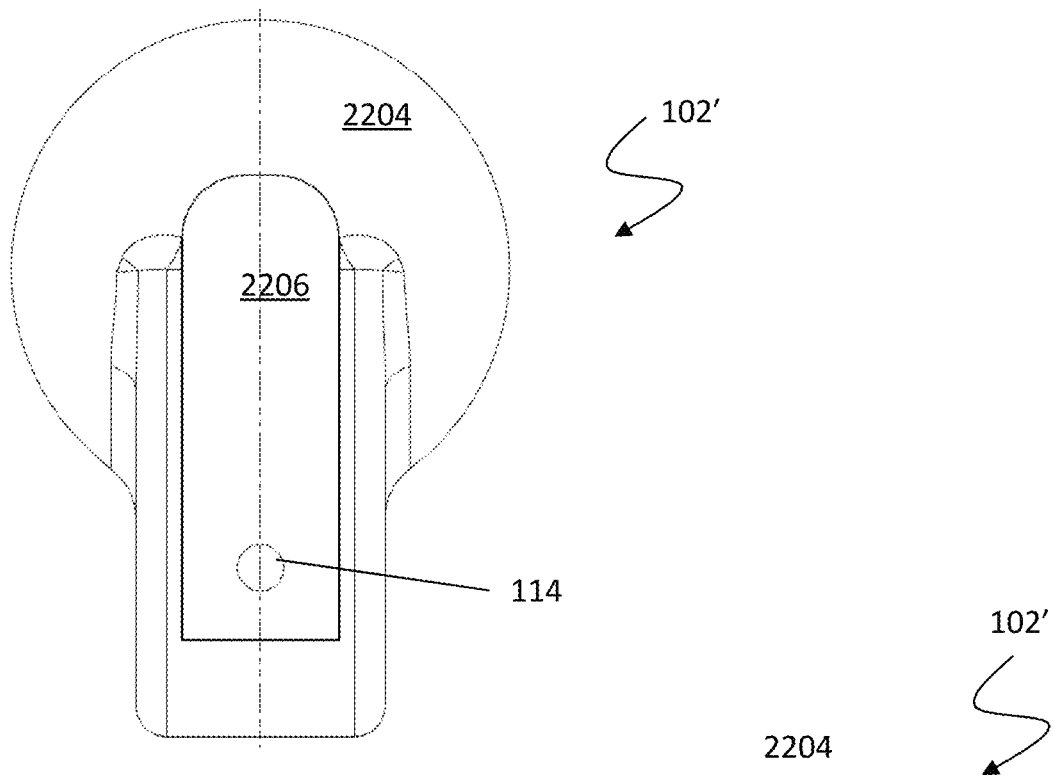
FIGS. 22A and 22B are schematic illustrations of an alternative exposure container shield according to an embodiment of the system described herein.
Figure 22B:
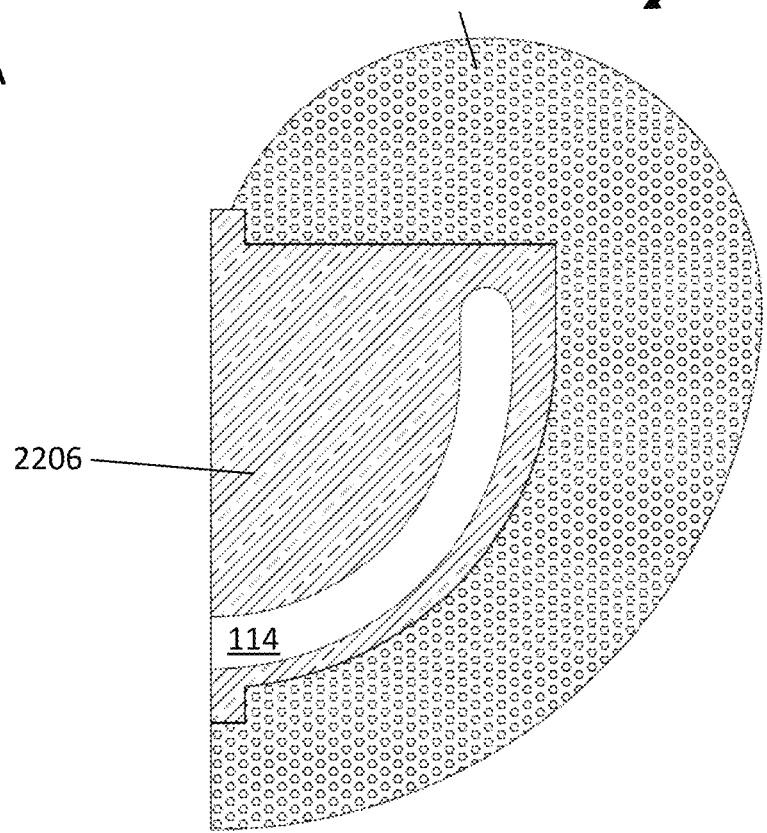

Referring to FIGS. 22A and 22B, an alternative embodiment of an exposure container 102' includes the J-channel 114, which is described elsewhere herein. The exposure container 102' also includes a body 2204 and an insert 2206 that fits into the body 2204 (i.e., the body 2204 accommodates the insert 2206). The insert 2206 contains the J-channel 114. In some embodiments, it is possible for the insert 2206 to be provided in multiple parts 2206. In use, the insert 2206 may be replaced when necessary without needing to replace the body 2204 since the body 2204 and the insert 2206 are separate components. The insert 2206 and the body 2204 together form the exposure container 102' that shields radiation from a source (not shown). Thus, after a number of uses in which the J-channel 114 becomes worn, the insert 2206 may be discarded and replaced with a new insert while the body 2204 remains. In an embodiment herein, the body 2204 is made of depleted uranium while the insert 2206 is made of tungsten, although of course other suitable materials may be used.

Various embodiments discussed herein may be combined with each other in appropriate combinations in connection with the system described herein. Additionally, in some instances, the order of steps in described flow processing may be modified, where appropriate. Further, various aspects of the system described herein may be implemented using software, hardware, a combination of software and hardware and/or other computer-implemented modules or devices having the described features and performing the described functions.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A radiography camera system, comprising:
   an exposure container made from radiation shielding material and having a curved channel therein that terminates inside the exposure container;
   a first conduit portion having a first end coupled to the exposure container;
   a switch coupled to a second end the first conduit portion;
   a second conduit portion having a first end coupled to the switch;
   a guide tube coupled to the switch;
   a crank coupled to a second end of the second conduit portion; and
   a cable disposed in the crank and having one of: a source assembly or a connector for a source assembly on an end thereof, the switch being actuated by at least one of: the connector for the source assembly or a component of the source assembly to cause the cable to feed through one of: the first conduit portion or the guide tube when the crank unwinds the cable.

2. The radiography camera system of claim 1, wherein the exposure container is made from at least one of: depleted uranium, tungsten, or lead.

3. The radiography camera system of claim 1, wherein the curved channel is J-shaped.

4. The radiography camera system of claim 1, wherein the switch has a first opening that accepts the cable from the second conduit portion, a second opening coupled to the first conduit portion and a third opening coupled to the guide tube.

5. The radiography camera system of claim 4, wherein winding the cable through the second hole toward the crank actuates the switch to cause the cable to feed through the third hole when the cable is unwound and wherein winding the cable through the third hole toward the crank actuates the switch to cause the cable to feed through the second hole when the cable is unwound.

6. The radiography camera system of claim 5, wherein, in response to tension from winding the cable, a portion of the switch rotates to actuate the switch by feeding the cable through the second hole or the third hole.

7. The radiography camera system of claim 1, further comprising:
   a ramp, proximal to a terminal end of the channel, the ramp allowing a portion of the source assembly to pass into the channel and preventing the portion of the source assembly from being removed from the channel; and
   a push bar that manually engages the ramp to allow the portion of the source assembly to be removed from the channel.

8. The radiography camera system of claim 1, further comprising:
   a pivot bar disposed inside the channel and having a hooked portion that engages a first portion of the source assembly when the source assembly is inserted into the channel to cause a second portion of the source assembly to pivot the pivot bar.

9. The radiography camera system of claim 1, wherein the source assembly includes a radioactive source, a connector that connects the source assembly to the cable, and a plurality of beads, disposed on the cable between the radioactive source and the connector, the beads providing radioactive shielding.

10. The radiography camera system of claim 9, wherein the beads are fixedly attached to the cable.

11. The radiography camera system of claim 9, wherein the beads are strung loosely on the cable.

12. The radiography camera system of claim 11, wherein the source assembly further includes a plurality of springs disposed between the beads to maintain spacing therebetween.

13. The radiography camera system of claim 12, wherein the source assembly further includes a first stop fixedly attached to the cable proximal to the radioactive source and a second stop fixedly attached to the cable proximal to the connector.

14. The radiography camera system of claim 9, wherein the beads are made from at least one of: depleted uranium, tungsten, or lead.

15. The radiography camera system of claim 9, wherein the source assembly is removably attached to the cable.

16. The radiography camera system of claim 1, further comprising:
   a portion separate from the exposure container and made from radiation shielding material, the portion accommodating the exposure container to form a shield that blocks radiation.

17. The radiography camera system of claim 16, wherein the portion is made of depleted uranium.

* * * * *